US009746475B2

(12) United States Patent
Arnold et al.

(10) Patent No.: US 9,746,475 B2
(45) Date of Patent: Aug. 29, 2017

(54) ANTIBODY AND ANTIBODY MIMETIC FOR VISUALIZATION AND ABLATION OF ENDOGENOUS PROTEINS

(75) Inventors: Don B. Arnold, Santa Monica, CA (US); Richard W. Roberts, South Pasadena, CA (US); Garrett G. Gross, Los Angeles, CA (US); Rudy Mora, Pasadena, CA (US); Jason Junge, South Pasadena, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 14/004,879

(22) PCT Filed: Mar. 13, 2012

(86) PCT No.: PCT/US2012/028947
§ 371 (c)(1),
(2), (4) Date: Apr. 22, 2014

(87) PCT Pub. No.: WO2012/125652
PCT Pub. Date: Sep. 20, 2012

(65) Prior Publication Data
US 2014/0287426 A1    Sep. 25, 2014

Related U.S. Application Data

(60) Provisional application No. 61/452,535, filed on Mar. 14, 2011, provisional application No. 61/532,065, filed on Sep. 7, 2011.

(51) Int. Cl.
| | | |
|---|---|---|
| C07H 21/04 | (2006.01) | |
| C12N 15/62 | (2006.01) | |
| G01N 33/58 | (2006.01) | |
| C07K 14/78 | (2006.01) | |
| C07K 16/18 | (2006.01) | |
| C07K 16/40 | (2006.01) | |
| C07H 21/02 | (2006.01) | |
| C12N 15/09 | (2006.01) | |

(52) U.S. Cl.
CPC .......... *G01N 33/581* (2013.01); *C07K 14/78* (2013.01); *C07K 16/18* (2013.01); *C07K 16/40* (2013.01); *C12N 15/62* (2013.01); *G01N 33/582* (2013.01); *C07K 2317/80* (2013.01); *C07K 2317/81* (2013.01); *C07K 2317/92* (2013.01); *C07K 2318/20* (2013.01); *C07K 2319/60* (2013.01); *C07K 2319/70* (2013.01); *C07K 2319/81* (2013.01)

(58) Field of Classification Search
None
See application file for complete search history.

(56) References Cited

U.S. PATENT DOCUMENTS

| | | |
|---|---|---|
| 5,955,593 A | 9/1999 | Korsmeyer |
| 6,207,446 B1 | 3/2001 | Szostak et al. |
| 6,214,553 B1 | 4/2001 | Szostak et al. |
| 6,258,558 B1 | 7/2001 | Szostak et al. |
| 6,261,804 B1 | 7/2001 | Szostak et al. |
| 6,281,344 B1 | 8/2001 | Szostak et al. |
| 6,518,018 B1 | 2/2003 | Szostak et al. |
| 7,011,972 B2 | 3/2006 | Barbas et al. |
| 7,270,950 B2 | 9/2007 | Szostak et al. |
| 2003/0220286 A1 | 11/2003 | Abruzzese et al. |
| 2004/0091878 A1 | 5/2004 | Sera |

FOREIGN PATENT DOCUMENTS

| | | |
|---|---|---|
| WO | WO 2010/124157 A1 | 10/2010 |
| WO | WO 2011/000929 A1 | 1/2011 |

OTHER PUBLICATIONS

Buijs et al., "The MN!-TEL Fusion Protein, Encoded by the Translocation (12;22)(p13;q11) in Myeloid Leukemia, is a Transcription Factor with Transforming Ability" 20(24) Molecular and Cellular Biology 9281-9293 (2000).*
Grignani et al., "Fusion proteins of the retinoic acid receptor-α recruit histone deacetylase in promyelocytic leukaemia" 391 Nature 815-818 (1998).*
Pengue et al., "Repression of transcriptional ativity at a distance by the evolutionarily conservedKRAB domain present in a subfamily of zinc finger proteins" 22(15) Nucleic Acids Research 2908-2914 (1994).*
Yaghmai et al. "Optimized Regulation of Gene Expression Using Artificial Transcription Factors" 5(6) Molecular Therapy 685-694 (2002).*
Hong et al., "GRIP1, a novel mouse protein that serves as a transcriptional coactivator in yeast for the hormone binding domains of steroid receptors" 93 Proceedings o fthe National Academy of Sciences USA 4948-4952 (1996).*
Witzgall, R. et al. (1994) "The Kruppel-associated box-Z (KRAB-A) domain of zinc finger proteins mediates transcriptional repression," Proc. Natl. Acad. Sci, 91:4514-4518.
International Search Report (ISA/KR) for International Application No. PCT/US2012/028947, mailed Nov. 28, 2012, 5 pages.
Andersson A M et al. (1997), "A retention signal necessary and sufficient for Golgi localization maps to the cytoplasmic tail of a Bunyaviridae (Uukuniemi virus) membrane glycoprotein", Journal of Virology, vol. 71, No. 6, p. 4717-4727.
(Continued)

*Primary Examiner* — Nancy J Leith
(74) *Attorney, Agent, or Firm* — Foley & Lardner LLP; Antoinette F. Konski; Peng Sun

(57) ABSTRACT

Provided are compositions and methods for labeling an endogenous protein, in particular, in a live cell, or for ablating an endogenous or target protein. The compositions relate to a fusion protein having a binding moiety such as an antibody, an antigen binding fragment of an antibody or an antibody mimetic that recognizes the endogenous or target protein.

37 Claims, 29 Drawing Sheets

(56) References Cited

OTHER PUBLICATIONS

Aravind L et al. (2000), "The U box is a modified RING finger—a common domain in ubiquitination", Curr Biol, 10: R132-R134.

Bordallo J et al. (1998), "Der3p/Hrd1p is required for endoplasmic reticulum-associated degradation of misfolded lumenal and integral membrane proteins", Mol Biol Cell, 9: 209-222.

Colbran R J et al. (2004), "Calcium/calmodulin-dependent protein kinase II and synaptic plasticity", Curr Opin Neurobiol, 14(3): 318-327.

Corse E et al. (2002), "The cytoplasmic tail of infectious bronchitis virus E protein directs Golgi targeting", J Virol, 76(3): 1273-1284.

Dunn R et al. (2004), "The C2 domain of the RspS ubiquitin ligase binds membrane phosphoinositides and directs ubiquitination of endosomal cargo", J Cell Biol, 165: 135-144.

Fritschy J M et al. (2008), "Gephyrin: where do we stand, where do we go?", Trends Neurosci, 31(5): 257-264.

Funke L et al. (2005), "Membrane-associated guanylate kinases regulate adhesion and plasticity at cell junctions", Annu Rev Biochem, 74:219-245.

Giniger E et al. (1985), "Specific DNA binding of GAL4, a positive regulatory protein of yeast", Cell 40: 767-774.

Haigis M C et al. (2002), "KFERQ sequence in ribonuclease A-mediated cytotoxicity", J Biol Chem, 277: 11576-11581.

Huibregtse J M et al. (1995), "A family of proteins structurally and functionally related to the E6-AP ubiquitin-protein ligase", Proc Natl Acad Sci USA, 92: 2563-2567.

Koide A et al. (1998), "The fibronectin type III domain as a scaffold for novel binding proteins", J Mol Biol, 284: 1141-1151.

Liston P et al. (1996), "Suppression of apoptosis in mammalian cells by NAIP and a related family of IAP genes", Nature 379: 349-353.

McGee A W et al. (2001), "Structure of the SH3-guanylate kinase module from PSD-95 suggests a mechanism for regulated assembly of MAGUK scaffolding proteins", Mol Cell, 8(6): 1291-1301.

Roberts R W et al. (1997), "RNA-peptide fusions for the in vitro selection of peptides and proteins", Proc Natl Acad Sci USA, 94: 12297-12302.

Rosenberg O S et al. (2006), "Oligomerization states of the association domain and the holoenyzme of Ca2 /CaM kinase II", FEBS J., 273(4): 682-694.

Sola M et al. (2001), "X-ray crystal structure of the trimeric N-terminal domain of gephyrin", J. Biol. Chem., 276(27): 25294-25301.

Takahashi T T et al. (2003), "mRNA display: ligand discovery, interaction analysis and beyond", Trends Biochem Sci., 28(3): 159-165.

Tao H et al. (2008), "Structure of the MID1 tandem B-boxes reveals an interaction reminiscent of intermolecular ring heterodimers", Biochemistry, 47: 2450-2457.

Tsai D E et al. (1991), "U1-snRNP-A protein selects a ten nucleotide consensus sequence from a degenerate RNA pool presented in various structural contexts", Nucleic Acids Research, 19: 4931-4936.

Yang Z et al. (2010), "Mammalian autophagy: core molecular machinery and signaling regulation", Curr Opin Cell Biol, 22: 124-131.

\* cited by examiner

SEQUENCE LISTING

```
<160> NUMBER OF SEQ ID NOS: 1

<210> SEQ ID NO 1
<211> LENGTH: 5
<212> TYPE: PRT
<213> ORGANISM: Unknown
<220> FEATURE:
<223> OTHER INFORMATION: Description of Unknown: protein degradation
      signal peptide

<400> SEQUENCE: 1

Lys Phe Glu Arg Gln
1               5
```

US 9,746,475 B2

ANTIBODY AND ANTIBODY MIMETIC FOR VISUALIZATION AND ABLATION OF ENDOGENOUS PROTEINS

CROSS-REFERENCE TO RELATED APPLICATIONS

This application is a national stage application under 35 U.S.C. §371 of International Application No. PCT/US2012/028947 filed Mar. 13, 2012 which in turn claims priority under 35 U.S.C. §119(e) of U.S. Provisional Application Nos. 61/452,535 and 61/532,065, filed Mar. 14, 2011 and Sep. 7, 2011, respectively, the contents of each of which are incorporated by reference into the present disclosure.

STATEMENT OF GOVERNMENT SUPPORT

This invention was made with government support under Contract No. GM 083898 awarded by the National Institutes of Health and National Institute of General Medical Sciences. The government has certain rights to the invention.

FIELD OF INVENTION

The present disclosure generally relates to compositions and methods for visualization and ablation of endogenous proteins.

BACKGROUND OF THE INVENTION

Throughout and within this application various technical and patent literature are referenced either explicitly or by reference to an Arabic numeral. The bibliographic citations for the Arabic numeral citations are found after the experimental examples. The contents of these technical and patent citations are incorporated by reference into this application to more fully describe the state of the art to which this invention pertains.

To date, visualization of proteins inside cells has been addressed in two distinct fashions, each with its own considerable limitations: 1) by creating fusions with fluorescent proteins, and 2) by labeling the endogenous proteins with antibodies after killing the cell and immobilizing the cellular components.

Green fluorescent protein (GFP) and other fluorescent protein variants provide a way to visualize specific proteins in cells as GFP-target protein fusions. These protein fusions can be inserted into cells directly (e.g., by transfection or microinjection) or by complex genetic manipulations such as mouse knock-ins that enable replacement of the endogenous copy with the GFP-labeled copy. Direct insertion into cells by transfection often results in non-physiologic overexpression of protein that can alter both the target proteins subcellular localization and cellular morphology. Construction of knockin mice is labor- and time-intensive and offers no opportunity to label the target protein in a conformation, complex, or modification-selective fashion.

Antibodies can be useful for labeling and visualizing cellular components. This utility is derived from the fact that antibodies can selectively recognize biopolymers such as proteins, RNA, DNA, oligosaccharides, and complexes thereof. With regards to protein targeting, antibodies can recognize specific protein sequences (linear epitopes), protein surfaces (3-dimensional epitopes), protein conformations (e.g., activated vs. inactivated), protein complexes, and proteins bearing posttranslational modifications.

For visualization, however, antibodies are traditionally deployed by using fixed cells—dead cells that have had the membrane portion stripped off and the protein components fused together via addition of cross-linking reagents. Antibodies can also be utilized to label tissues that have been frozen and sectioned, destroying the original tissue.

Recently, it has been shown that antibodies can be microinjected into cells and used for visualization. However, this approach is suboptimal as it requires injection of every cell to be visualized, is transient, has limited dosage control over the injection, and because the antibodies themselves will gradually be inactivated/degraded by the reducing environment inside the cell and cellular protein turnover. Furthermore, the amount of antibody in the cell must match exactly the amount of target, something that is not currently possible, either the target is not sufficiently labeled, or there is a high level of background label.

Currently there is no method for directly degrading specific endogenous proteins. Current methods such as siRNA target mRNA and thus protein elimination is indirect. Drawbacks of siRNA include but are not limited to several issues. The first is the fact that in siRNA, protein is not degraded, but production of protein is blocked, and thus elimination of protein depends on the protein turnover rate. As a result elimination of more than half of the protein can take over 2 weeks. The second is that in siRNA, there can be "off target" effects that result in blocking protein production from unintended RNA templates. A third limitation is that siRNA targets all proteins encoded by particular mRNAs. Thus all mRNAs containing the same nucleotide sequence are affected. This limitation makes it impossible to target proteins with specific conformations (e.g., activated or inactivated forms of the protein) or specific post-translational modifications that have the same mRNA sequence. This limitation also may make it difficult to target/avoid various splice variants from a particular gene. With regards to oncogenes and oncogeneic mutations, siRNA methods are also limited in targeting specific sites that differ from the wildtype gene sequence by one or a small number of nucleotides.

SUMMARY OF THE INVENTION

The present disclosure provides, in one embodiment, compositions and methods for labeling an endogenous protein in a living cell. The composition can be in the form of a polynucleotide encoding a fusion protein that includes a first portion or binding moiety for recognizing the endogenous protein, an optional second portion for emitting a signal, and a third portion that regulates the expression of the fusion protein itself, by virtue of binding to a transcription regulatory element that is operatively linked to the coding sequence. As illustrated in FIG. 1, when the amount of expressed fusion protein exceeds what is required for binding all of the endogenous protein in the cell, the fusion protein binds to the transcription regulatory element and shuts down the expression of itself. As such, no extra fusion protein is expressed in the cell other than those bound to the target protein, eliminating background noise. It does not require integration into the genome—therefore no health-related position effect. The compositions also allow for cell-specific expression in any animal. Transcriptional control can be used for any protein that binds at high affinity to a membrane protein or membrane associated protein.

Also provided is a fusion protein that includes a first portion or binding moiety for recognizing an endogenous protein and a second portion that directs the fusion protein, along with the bound endogenous protein, to a protein degradation pathways, such as through ubiquitination, lysomosal degradation or autophagy (see illustration in FIG. 2). By introducing the fusion protein, or a polynucleotide encoding the fusion protein to a cell, the fusion protein can then effectively recognize the target endogenous protein and effect its removal in the cell.

Also provided is a system for the expression of two or more polynucleotides, the system comprising, or alternatively consisting essentially of, or yet further consisting of a polynucleotide as described herein and a second nucleic acid sequence encoding a fusion polypeptide comprising, or alternatively consisting essentially of, or yet further consisting of, (a) a minimal promoter and (b) a transcription factor that mediates expression of the binding moiety and (c) a heterologous protein, wherein the transcription factor regulates the minimal promoter causing expression of the heterologous protein.

Various types of proteins or protein fragments can be used as the binding moiety or portion in the above embodiments, including but not limited to, antibodies, antigen binding fragments of antibodies, antibody mimetics such as intrabodies. They can be selected or prepared with known methods in the art to specifically recognize any target protein.

Further provided are methods for testing the binding specificity and efficiency of a binding protein, such as an antibody, an antigen binding fragment of an antibody, or an antibody mimetic, to an endogenous protein, in particular intracellularly. Such methods provide a fusion protein that includes the domain of the target protein that is recognized by the binding protein and a peptide that localizes the fusion protein to a specific location, such as an organelle membrane. In the event the binding protein, upon binding to the target protein, is located properly, it is shown that the binding protein works specifically and efficiently.

Thus, in one embodiment, the present disclosure provides a polynucleotide comprising, or alternatively consisting essentially of, or alternatively consisting, (1) a nucleic acid sequence encoding a fusion polypeptide comprising (a) a binding moiety as described herein, e.g., an antibody, an antigen binding fragment of an antibody or an antibody mimetic and (b) a transcription factor and (2) a transcription regulatory element operatively linked to the nucleic acid sequence, wherein the transcription regulatory element regulates the transcription of the binding moiety and the transcription factor regulates the activity of the transcription regulatory element.

In one aspect, the binding moiety is one or more of an antibody, an antibody fragment, an antibody mimetic, an intrabody, a monobody, a linear peptide, a lipocalin scaffold, an affibody scaffold or a DARPin scaffold. In another aspect, the intrabody comprises a fibronectin peptide. In a particular aspect, the fibronection peptide comprises a 10FnIII fragment.

In one aspect, the transcription factor comprises a DNA binding domain. In another aspect, the transcription factor is selected from Gal4, LexA or a zinc finger domain, and optionally further comprises a regulatory domain, e.g., a transcriptional control system, a transcriptional activator or an inducible promoter. The transcription factor, in some aspects, comprises a DNA binding domain of Gal4 and a regulatory domain of Krab(A).

In any of the above embodiments, the fusion polypeptide further comprises a reporter, such as, but not limited to a green fluorescent protein (GFP), a blue fluorescent protein (BFP), a cyan fluorescent protein (CFP), a yellow fluorescent protein (YFP), mCherry, dTomato, mPlum, mOrange, mCitrine, Ypet, Cerulean CFP, luciferase, or β-galactosidase.

The binding moiety, e.g., an antibody, the antigen binding fragment or the antibody mimetic, in some aspects, specifically recognizes an endogenous or target protein in a cell. The endogenous or target protein can be a transmembrane protein, a nucleic protein, a cytoplasmic protein, a secreted protein, or an organelle protein. In one aspect, the protein is a transmembrane protein.

Also provided are polypeptides encoded by the polynucleotide, the system, DNA constructs comprising such a polynucleotide or polynucleotides, and a vector, a composition comprising such a polynucleotide, polynucleotides and a carrier, or a cell comprising any of the above.

The present disclosure, in another embodiment, provides a method for labeling an endogenous protein in a cell, comprising contacting the cell with a polynucleotide comprising (1) a nucleic acid sequence encoding a fusion polypeptide comprising (a) a binding moiety such as an antibody, an antigen binding fragment of an antibody or an antibody mimetic, (b) a reporter and (c) a transcription factor and (2) a transcription regulatory element operatively linked to the nucleic acid sequence, wherein the transcription regulatory element regulates the transcription of the binding moiety and the transcription factor regulates the activity of the transcription regulatory element, and wherein the binding moiety specifically recognizes the endogenous protein.

Also provided, in one embodiment, is a polynucleotide comprising, or alternatively consisting essentially of, or alternatively consisting, a nucleic acid sequence encoding a fusion polypeptide comprising (a) a binding moiety such as an antibody, an antigen binding fragment of an antibody or an antibody mimetic and (b) a protein degradation signal.

In one aspect, the binding moiety such as an antibody, the antigen binding fragment or the antibody mimetic specifically recognizes an endogenous protein in a cell. The antibody mimetic, in some aspects, comprises an intrabody, a monobody, a linear peptide, a lipocalin scaffold, an affibody scaffold or a DARPin scaffold. In one aspect, the intrabody comprises a fibronectin peptide. In a particular aspect, the fibronection peptide comprises a 10FnIII fragment.

In some aspects, the protein degradation signal induces protein degradation of a polypeptide encoded by the polynucleotide. In yet another aspect, the protein degradation is through ubiquitination, lysosomal degradation, or autophagy. In one particular aspect, the protein degradation is through ubiquitination.

In one aspect, the protein degradation signal comprises a ubiquitin ligase, a HECT domain of an E6 protein, C20-WW-HECT, a Ring domain of Der3/Hrd1, a B-box domain of a TRIM protein, a U-box domain, KFERQ, Arg12 or Atg8/LC3.

In another aspect, the ubiquitin ligase comprises one or more of a Ring domain of a protein X-linked mammalian inhibitor of apoptosis (XIAP) or of a mammalian Double Minute 2 protein, e.g., a Human Double Minute 2 ("HDM2") or mouse Double Minute 2 ("Mdm2").

Also provided are polypeptides encoded by the polynucleotide, DNA constructs comprising such a polynucleotide, polynucleotides, the system, and a vector, a composition comprising such a polynucleotide and a carrier, or a cell comprising any of the above.

Further provided is a method for inhibiting an activity of or degrading an endogenous protein in a cell, comprising contacting the cell with a polynucleotide comprising a nucleic acid sequence encoding a fusion polypeptide comprising (a) a binding moiety such as an antibody, an antigen binding fragment of an antibody or an antibody mimetic and (b) a protein degradation signal, wherein the binding moiety such as an antibody, the antigen binding fragment or the antibody mimetic specifically recognizes the endogenous protein.

Yet in another embodiment, the present disclosure provides a method for treating a disease characterized by expression of an endogenous protein in a cell, comprising contacting the cell with a polynucleotide comprising a nucleic acid sequence encoding a fusion polypeptide comprising (a) a binding moiety such as an antibody, an antigen binding fragment of an antibody or an antibody mimetic and (b) a protein degradation signal, wherein the binding moiety such as an antibody, the antigen binding fragment or the antibody mimetic specifically recognizes the endogenous protein.

In one aspect, the endogenous protein is selected from Tau, alpha-Synuclein, prion protein, Huntingtun, Nav1.7, CCR5, HER-2, EGFR, Estrogen receptor, an oncogenes, or a drug resistant gene.

Still further in one embodiment, provided is a composition comprising, or alternatively consisting essentially of, or alternatively consisting, (1) a first polynucleotide encoding a fusion polypeptide comprising a binding moiety such as an antibody, an antigen binding fragment of an antibody or an antibody mimetic and a reporter and (2) a second polynucleotide encoding a fusion polypeptide comprising a target peptide sequence and a cell localization domain, wherein the binding moiety such as an antibody, the antigen binding fragment or the antibody mimetic specifically recognizes the target peptide sequence.

Also provided is a kit comprising, or alternatively consisting essentially of, or alternatively consisting, (1) a first polynucleotide encoding a fusion polypeptide comprising a binding moiety such as an antibody, an antigen binding fragment of an antibody or an antibody mimetic and a reporter and (2) a second polynucleotide encoding a fusion polypeptide comprising a target peptide sequence and a cell localization domain, wherein the binding moiety such as an antibody, the antigen binding fragment or the antibody mimetic specifically recognizes the target peptide sequence.

In one aspect, the antibody mimetic comprises an intrabody, a monobody, a linear peptide, a lipocalin scaffold, an affibody scaffold or a DARPin scaffold. In another aspect, the intrabody comprises a fibronectin peptide. In yet another aspect, the fibronection peptide comprises a 10FnIII fragment.

In one aspect, the cell localization domain localizes the chimeric polypeptide at Golgi apparatus, endoplasmic reticulum, lysosome, mitochondria, plasma membrane, or apical or basolateral domain of an epithelial cell.

In another aspect, the reporter comprises a green fluorescent protein (GFP), a blue fluorescent protein (BFP), a cyan fluorescent protein (CFP), a yellow fluorescent protein (YFP), mCherry, dTomato, mPlum, mOrange, mCitrine, Ypet, Cerulean CFP, luciferase, or β-galactosidase.

DETAILED DESCRIPTION OF THE DISCLOSURE

Figure 1:
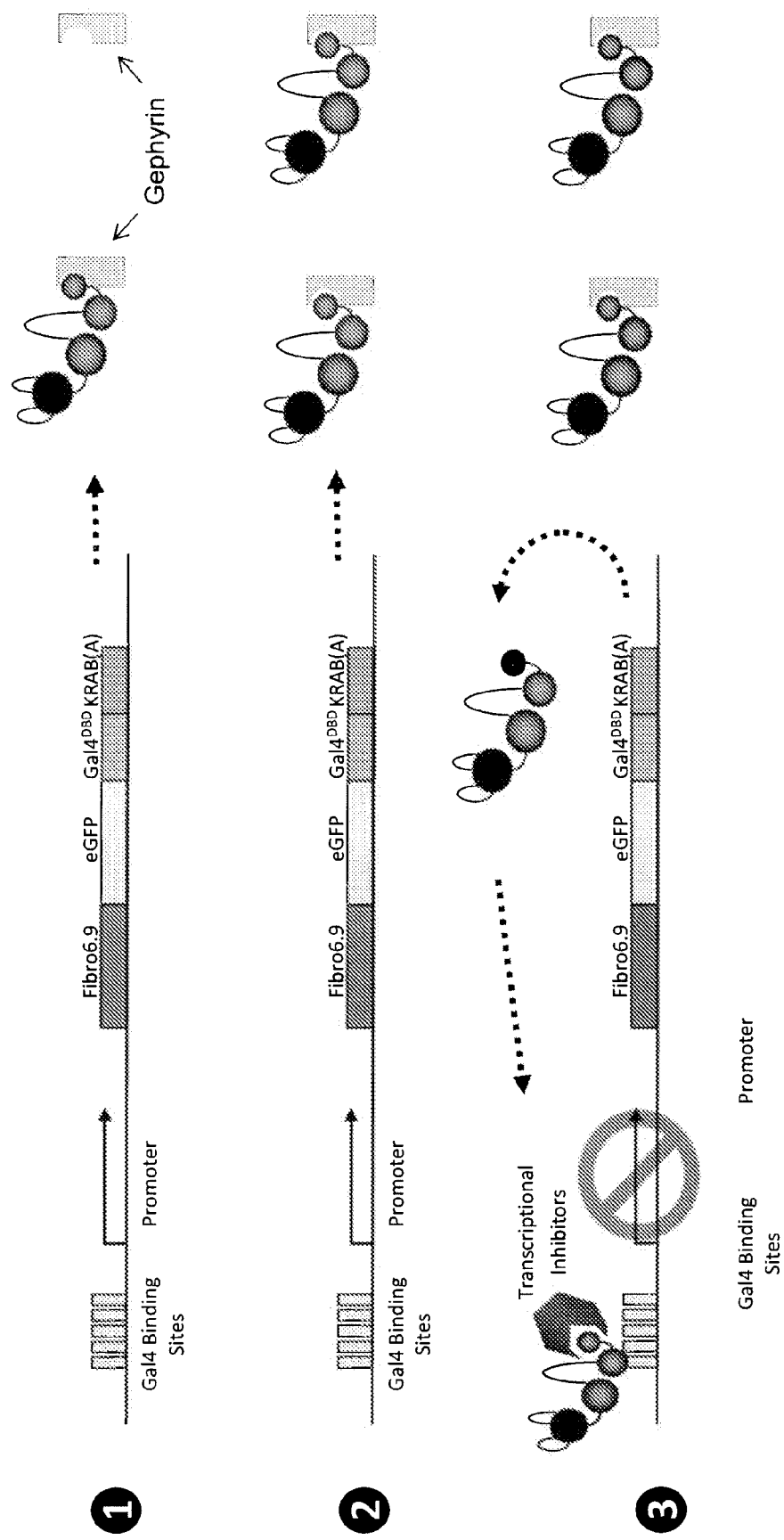
FIG. 1 illustrates a design of a polynucleotide where the expression of an intrabody is regulated so as not to exceed what is needed to bind the target protein (e.g., Gephryin).

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All technical and patent publications cited herein are incorporated herein by reference in their entirety. Nothing herein is to be construed as an admission that the invention is not entitled to antedate such disclosure by virtue of prior invention.

The practice of the present invention will employ, unless otherwise indicated, conventional techniques of tissue culture, immunology, molecular biology, microbiology, cell biology and recombinant DNA, which are within the skill of the art. See, e.g., Sambrook and Russell eds. (2001) Molecular Cloning: A Laboratory Manual, $3^{rd}$ edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, $5^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); and Herzenberg et al. eds (1996) Weir's Handbook of Experimental Immunology.

All numerical designations, e.g., pH, temperature, time, concentration, and molecular weight, including ranges, are approximations which are varied (+) or (−) by increments of 1.0 or 0.1, as appropriate. It is to be understood, although not always explicitly stated, that all numerical designations are preceded by the term "about". It also is to be understood, although not always explicitly stated, that the reagents described herein are merely exemplary and that equivalents of such are known in the art.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above.

As used in the specification and claims, the singular form "a", "an" and "the" include plural references unless the context clearly dictates otherwise. For example, the term "a pharmaceutically acceptable carrier" includes a plurality of pharmaceutically acceptable carriers, including mixtures thereof.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

A "subject" of this invention is a cell or an animal such as a mammal, or a human. Non-human animals subject to diagnosis or treatment are those in need of treatment such as for example, simians, murine, such as, rats, mice, canine, such as dogs, leporids, such as rabbits, livestock, sport animals, and pets.

The term "protein", "peptide" and "polypeptide" are used interchangeably and in their broadest sense to refer to a compound of two or more subunit amino acids, amino acid analogs or peptidomimetics. The subunits may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

The term "isolated" as used herein with respect to nucleic acids, such as DNA or RNA, refers to molecules separated from other DNAs or RNAs, respectively that are present in the natural source of the macromolecule. The term "isolated nucleic acid" is meant to include nucleic acid fragments which are not naturally occurring as fragments and would not be found in the natural state. The term "isolated" is also used herein to refer to polypeptides and proteins that are isolated from other cellular proteins and is meant to encompass both purified and recombinant polypeptides. In other embodiments, the term "isolated" means separated from constituents, cellular and otherwise, in which the cell, tissue, polynucleotide, peptide, polypeptide, protein, antibody or fragment(s) thereof, which are normally associated in nature. For example, an isolated cell is a cell that is separated from tissue or cells of dissimilar phenotype or genotype. As is apparent to those of skill in the art, a non-naturally occurring polynucleotide, peptide, polypeptide, protein, antibody or fragment(s) thereof, does not require "isolation" to distinguish it from its naturally occurring counterpart.

As used herein, the term "biological equivalent thereof" or "equivalent thereof" when referring to a reference protein, polypeptide or nucleic acid, intends those having minimal homology while still maintaining desired structure or functionality. Unless specifically recited herein, it is contemplated that any polynucleotide, polypeptide or protein mentioned herein also includes equivalents thereof. For example, an equivalent intends at least about 80% homology or identity and alternatively, at least about 85%, or alternatively at least about 90%, or alternatively at least about 95%, or alternatively 98% percent homology or identity and exhibits substantially equivalent biological activity to the reference protein, polypeptide or nucleic acid. Alternatively, an equivalent nucleic acid hybridizes to a reference polynucleotide or its complement under conditions of high stringency.

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by =HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present invention.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in an eukaryotic cell.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

A "composition" is intended to mean a combination of active agent and another compound or composition, inert (for example, a detectable agent or label) or active, such as an adjuvant.

A "pharmaceutical composition" is intended to include the combination of an active agent with a carrier, inert or active, making the composition suitable for diagnostic or therapeutic use in vitro, in vivo or ex vivo.

As used herein, the terms "treating," "treatment" and the like are used herein to mean obtaining a desired pharmacologic and/or physiologic effect. The effect may be prophylactic in terms of completely or partially preventing a disorder or sign or symptom thereof, and/or may be therapeutic in terms of a partial or complete cure for a disorder and/or adverse effect attributable to the disorder.

A "subject" of diagnosis or treatment is a cell or an animal such as a mammal, or a human. Non-human animals subject to diagnosis or treatment and are those subject to infections or animal models, for example, simians, murines, such as, rats, mice, chinchilla, canine, such as dogs, leporids, such as rabbits, livestock, sport animals, and pets.

"Administration" can be effected in one dose, continuously or intermittently throughout the course of treatment. Methods of determining the most effective means and dosage of administration are known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated, and target cell or tissue. Non-limiting examples of route of administration include oral administration, nasal administration, injection, and topical application.

As used herein, "stem cell" defines a cell with the ability to divide for indefinite periods in culture and give rise to specialized cells. Stem cells include, for example, somatic (adult) and embryonic stem cells and parthenogenic stem cells. A somatic stem cell is an undifferentiated cell found in a differentiated tissue that can renew itself (clonal) and (with certain limitations) differentiate to yield all the specialized cell types of the tissue from which it originated. An embryonic stem cell is a primitive (undifferentiated) cell derived from the embryo that has the potential to become a wide variety of specialized cell types. An embryonic stem cell is one that has been cultured under in vitro conditions that allow proliferation without differentiation. Non-limiting examples of embryonic stem cells are the HES2 (also known as ES02) cell line available from ESI, Singapore and the H1 (also know as WA01) cell line available from WiCells, Madison, Wis. In addition, for example, there are 40 embryonic stem cell lines that are recently approved for use in NIH-funded research including CHB-1, CHB-2, CHB-3, CHB-4, CHB-5, CHB-6, CHB-8, CHB-9, CHB-10, CHB-11, CHB-12, RUES1, HUES1, HUES2, HUES3, HUES4, HUES5, HUES6, HUES7, HUES8, HUES9, HUES10, HUES11, HUES12, HUES13, HUES14, HUES15, HUES16, HUES17, HUES18, HUES19, HUES20, HUES21, HUES22, HUES23, HUES24, HUES26, HUES27, and HUES28. Pluripotent embryonic stem cells can be distinguished from other types of cells by the use of markers including, but not limited to, Oct-4, alkaline phosphatase, CD30, TDGF-1, GCTM-2, Genesis, Germ cell nuclear factor, SSEA1, SSEA3, and SSEA4.

A "fusion" polypeptide refers to a polypeptide created through the joining of two or more coding sequences which originally coded for separate proteins. Translation of this fusion gene results in a single polypeptide with functional properties derived from each of the original proteins. In one aspect the polynucleotides and polypeptides that are "fused" are covalently attached.

As used herein, an "antibody" includes whole antibodies, any antigen binding fragment or a single chain thereof, or antibody mimetics. Thus the term "antibody" includes any protein or peptide containing molecule that comprises at least a portion of an immunoglobulin molecule or a peptide having similar structure and function. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein.

The antibodies can be polyclonal or monoclonal and can be isolated from any suitable biological source, e.g., murine, rat, sheep and canine.

The term "human antibody" as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody" as used herein, is not intended to include antibodies in which CDR sequences derived from the germline of another mammalian species, such as a mouse, have been grafted onto human framework sequences. Thus, as used herein, the term "human antibody" refers to an antibody in which substantially every part of the protein (e.g., CDR, framework, $C_L$, $C_H$ domains (e.g., $C_{H1}$, $C_{H2}$, $C_{H3}$), hinge, (VL, VH)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies include any combination of the above. Such changes or variations optionally and preferably retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

A "transcription factor" refers to a polypeptide or domain that binds to specific DNA sequences, thereby controlling the transcription of genetic information from DNA to mRNA.

A "transcription regulatory element" refers to a region of DNA or RNA that regulates the expression of genes located on that same molecule of DNA. A transcription regulatory elements is often the binding site for one or more transcription factors. A transcription regulatory elment may be located 5' to the coding sequence of the gene it controls (in the promoter region or further upstream), in an intron, or 3' to the gene's coding sequence, either in the untranslated or untranscribed region.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

Compositions and Methods for Labeling an Endogenous Protein

One embodiment of the present disclosure provides a polynucleotide encoding a binding moiety such as antibodies, antibody fragments or antibody mimetics for labeling an endogenous protein.

Traditionally, antibodies have been used to label and visualize endogenous proteins, however several properties drastically limit their utility: 1. Antibody staining of intracellular protein requires that tissue be fixed and permeabilized, and thus living cells in general cannot be stained. 2. The expression patterns associated with individual neurons in brain tissue are superimposed, which removes the context that is required for interpreting the localization pattern of a protein in a single cell.

Conversely, over-expressed, exogenous proteins with fluorescent protein tags can be visualized in living cells. They can also be expressed in sparsely distributed cells in intact tissue allowing easy interpretation of their expression patterns. However, in the vast majority of cases they do not localize in the same manner as their endogenous counterparts, likely because they must compete for interactors such as auxiliary subunits, motor proteins and cytoskeletal anchors.

Figure 4:
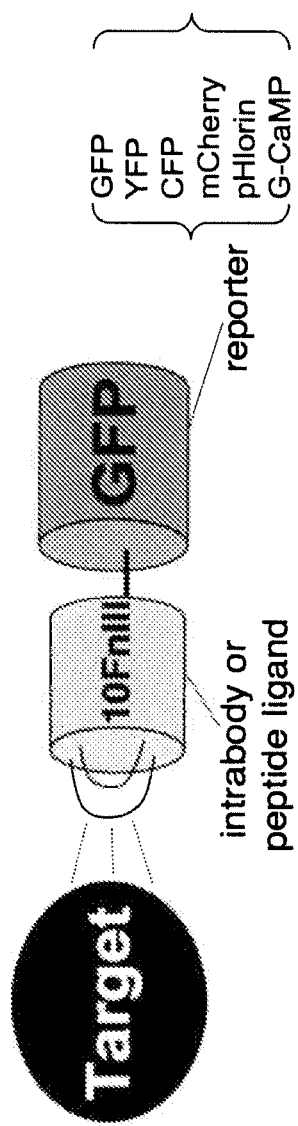
FIG. 4 shows the design of a molecule that behaves like an antibody, directly binding to the target protein, but that is genetically encoded so that its expression can be controlled and so that it can be fused to functional domains such as fluorescent tags. Intrabodies based on a 10fnIII scaffold and generated using mRNA display are linked to appropriate reporters to allow visualization of the target in cells such as neurons.

Applicants provide herein a binding moiety, e.g. a molecule that behaves like an antibody, directly binding to the target protein, but that is genetically encoded so that its expression can be controlled and so that it can be fused to functional domains such as fluorescent tags (FIG. 4).

For instance, referring to FIG. 1, an expression construct is prepared including an intrabody against Gephryine and a transcription factor is prepared by fusing the DNA binding domain GAL4 to the transcriptional inhibitor Krab(A). In addition, the construct also includes multiple GAL4 binding sites to the promoter. In another aspect, an intrabody against PSD-95 is provided.

When the intrabody is initially expressed in a cell, there is more endogenous Gephyrin than what is bound to intrabody. As the amount of synthesized intrabody increases gradually more and more of the endogenous target becomes bound until 100% of target is bound.

At that point the unbound transcription factor goes to the nucleus and turns of transcription. The result is that the amount of intrabody produced is precisely the same as that of the endogenous target and as a result there is no background.

Thus, in one embodiment, the present disclosure provides a polynucleotide comprising (1) a nucleic acid sequence encoding a fusion polypeptide comprising (a) a binding moiety such as an antibody, an antigen binding fragment of an antibody or an antibody mimetic and (b) a transcription factor and (2) a transcription regulatory element operatively linked to the nucleic acid sequence, wherein the transcription regulatory element regulates the transcription of the binding moiety and the transcription factor regulates the activity of the transcription regulatory element.

An antibody mimetic is an organic compound that, like conventional antibodies, can specifically bind antigens. An antibody mimetic can be an artificial peptide with a molar mass of about 3 to 20 kDa. In one aspect, an antibody mimetic is an intrabody.

An "intrabody" is an antibody that is expressed within a cell to bind to an intracellular protein. Methods of preparing an intrabody that specifically recognizes a target protein are known in the art and further described below and in experimental examples.

Figure 9:
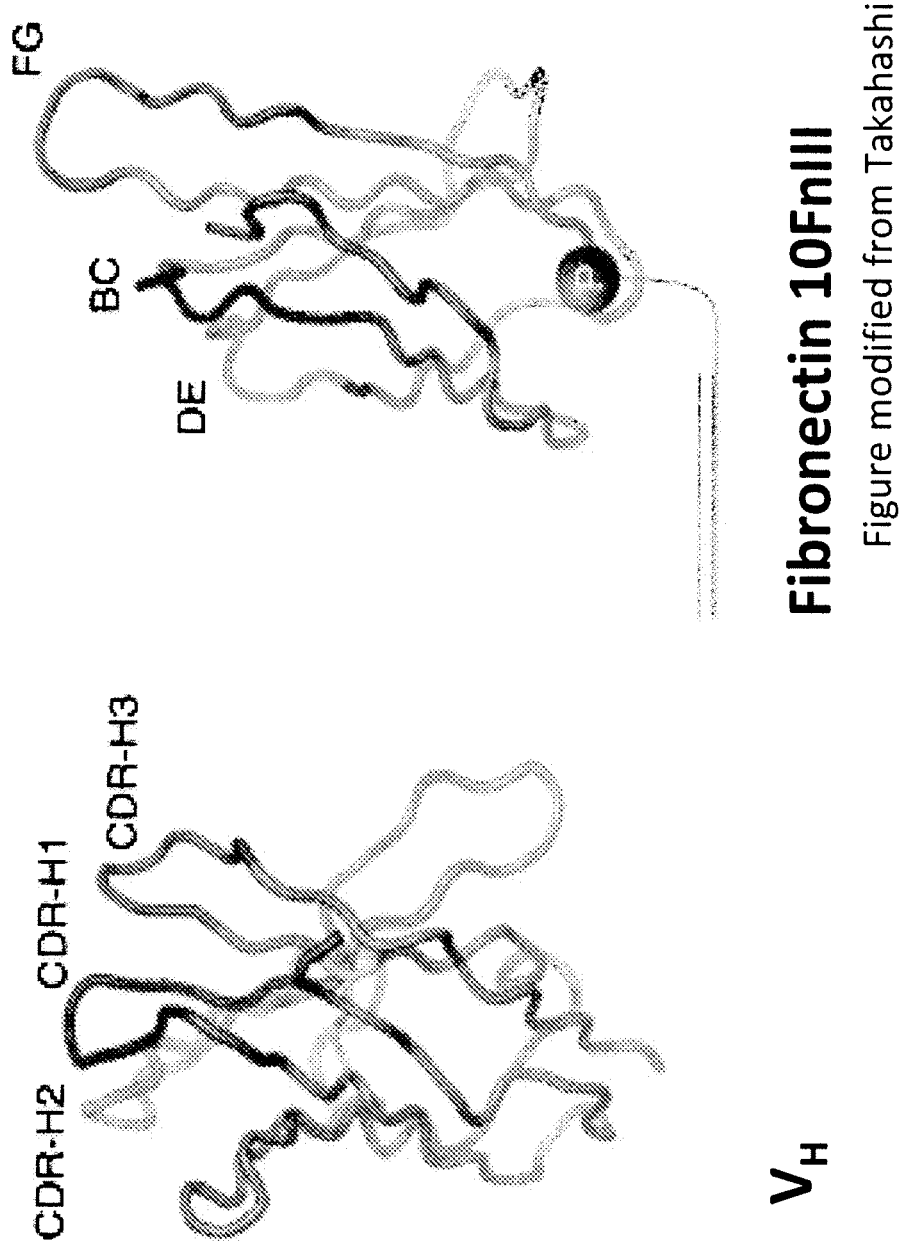
FIGS. 9A-B show that the 10FnIII domain of fibronectin (FIG. 9B), 10 fn III has a structure very similar to a camelid antibody (FIG. 9A), with three distinct external loops, however it has no disulphide bonds and thus is stable in the reduced environment of the cytoplasm. It is stable up to 95° C. The figure is adapted and modified from Takahashi T T et al. (2003), supra.

It would be readily appreciated in the art that any other binding moiety that could be used inside cells which have sufficient affinity and selectivity is an antibody suitable for this purpose. In this context, the binding moiety can be a polypeptide chain, or alternatively an engineered version of fibronectin 10FnIII (using the modified scaffold described in (Olson, C. A., et al. (2008) mRNA display selection of a high-affinity, modification-specific phospho-IkappaBalpha-binding fibronectin, ACS Chem Biol 3:480-485). This fibronectin domain is sometimes referred to as a monobody (Batori, V., et al. (2002) Exploring the potential of the monobody scaffold: effects of loop elongation on the stability of a fibronectin type III domain, Protein Eng 15:1015-1020). As illustrated in FIG. 9, 10FnIII is structurally similar to an antibody heavy chain.

A "monobody" also refers to a genetically engineered protein that is able to bind to antigens. Non-limiting examples include the monobody angiocept (CT-322), a VEGF receptor antagonist, for the treatment of glioblastoma (Bloom L, Calabro V (July 2009). "FN3: a new protein scaffold reaches the clinic," Drug Discov. Today 14 (19-20): 949-55).

A natural ligand or derivative of the ligand to an endogenous protein can also be used in place of the antibody, as it recognizes the endogenous protein.

An antibody, antibody fragment or antibody mimetic can be selected to target a specific domain in a target protein. In one aspect, the targeted domain is a multimerization domain. Mutlimerization domains tend to have rigid structures that make for very good binding sites.

Further, multimerization domains tend to have a single function: multimerization. Thus, if the intrabody binds the target protein after multimerization has occurred then there is no disruption of protein function.

Figure 10:
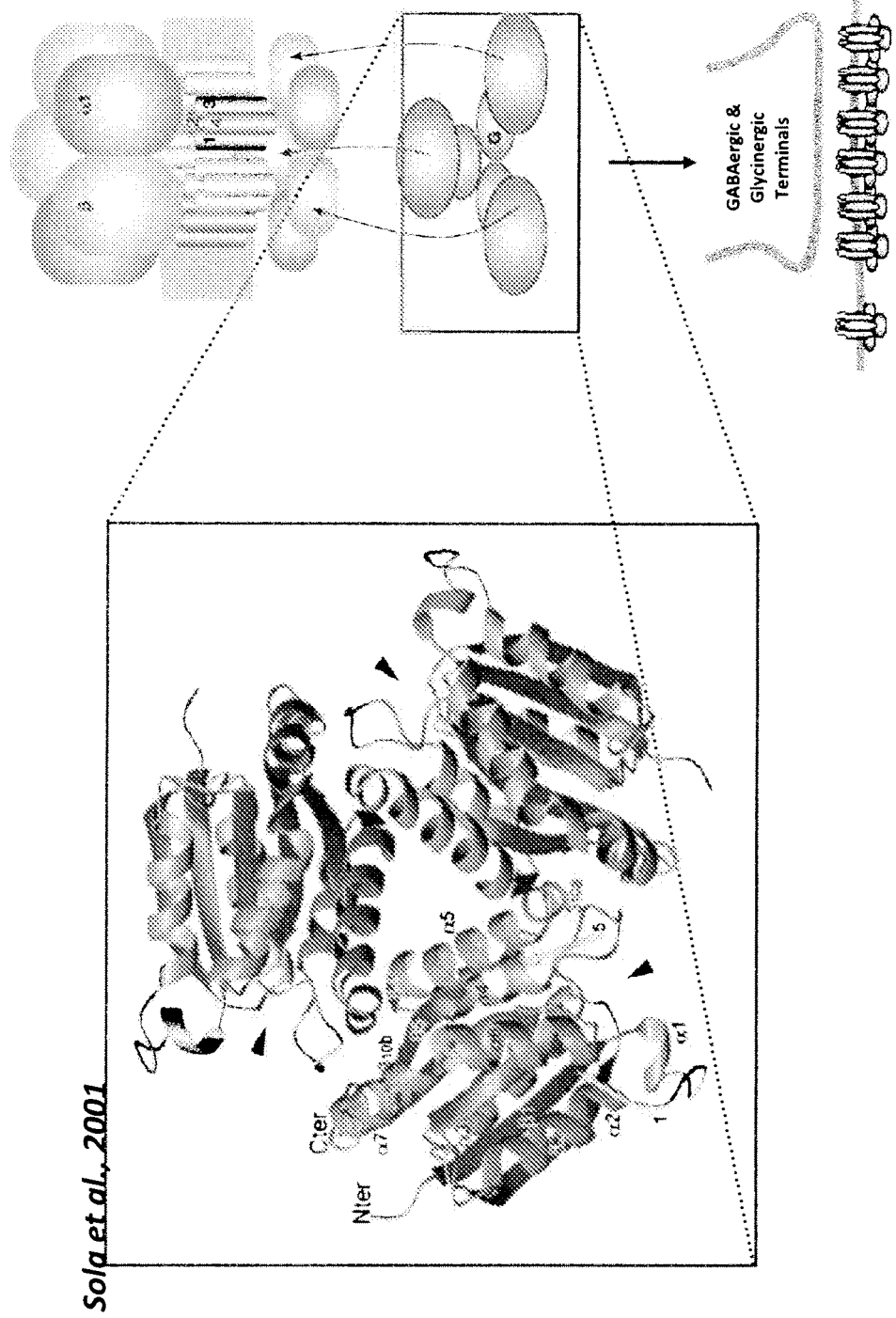
FIG. 10 shows the structures of a target endogenous protein, Gephrin. The intrabody targets the G domain of Gephyrin, which mediates trimerization. Gephryin is the scaffolding protein that binds to GABA and Glycine receptors. By virtue of the G domain and the E domain, which mediates dimerization, it forms a hexagonal structure that forms main support for postsynaptic inhibitory sites. This figure is adapted from Sola M, et al. (2001) "X-ray crystal structure of the trimeric N-terminal domain of gephyrin," J Biol Chem. 276(27):25294-301 and Fritschy J M et al. (2008) "Gephyrin: where do we stand, where do we go?" Trends Neurosci. May; 31(5):257-64.

In a non-limiting example, a targeted domain is the G domain of Gephyrin, which mediates trimerization (FIG. 10). Gephyrin is the scaffolding protein that binds to GABA and Glycine rsceptors. By virtue of the G domain and the E domain, which mediates dimerization, it forms a hexagonal structure that forms main support for postsynaptic inhibitory sites.

Figure 11:
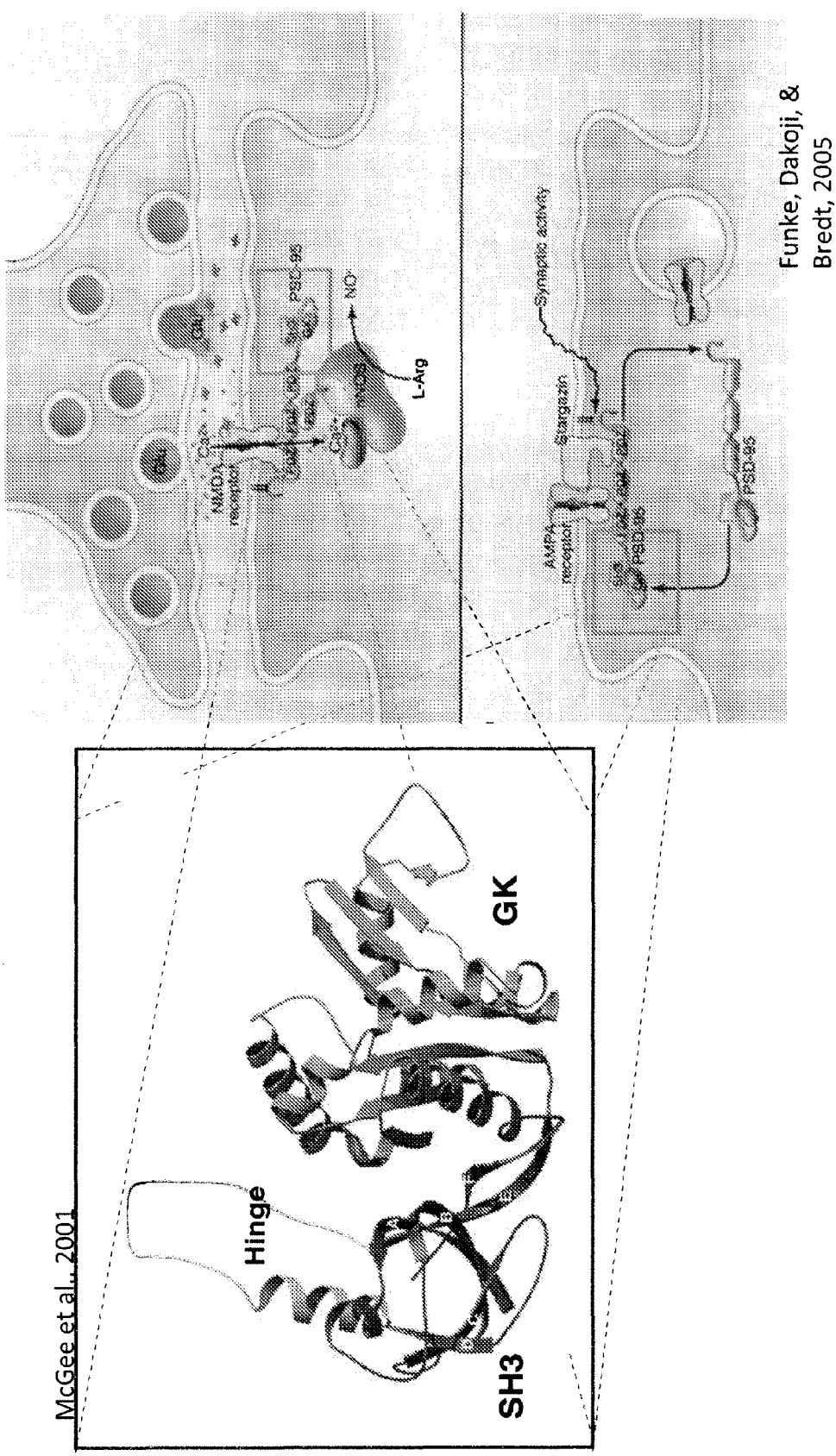
FIG. 11 shows the structure of another target endogenous protein, PSD-95. Here the target domain is the SH3-GK domain of PSD-95. Two of these domains can either form an intramolecular or intermolecular dimer. The latter can lead to rafting together of PSD-95. The intrabody can be made to bind either to the intramoleculer or intermolecular SH3-GK dimer. This figure is adapted from McGee A W et al (2001) "Structure of the SH3-guanylate kinase module from PSD-95 suggests a mechanism for regulated assembly of MAGUK scaffolding proteins," Mol Cell. 8(6):1291-301 and Funke L, et al. (2005) "Membrane-associated guanylate kinases regulate adhesion and plasticity at cell junctions," Annu Rev Biochem. 74:219-45.

Another example is the SH3-GK domain of PSD-95 (FIG. 11). Two such domains can either form an intramolecular or intermolecular dimer. The latter can lead to rafting together of PSD-95. Antibodies can be prepared that bind either to the intramoleculer or intermolecular SH3-GK dimer.

Figure 12:
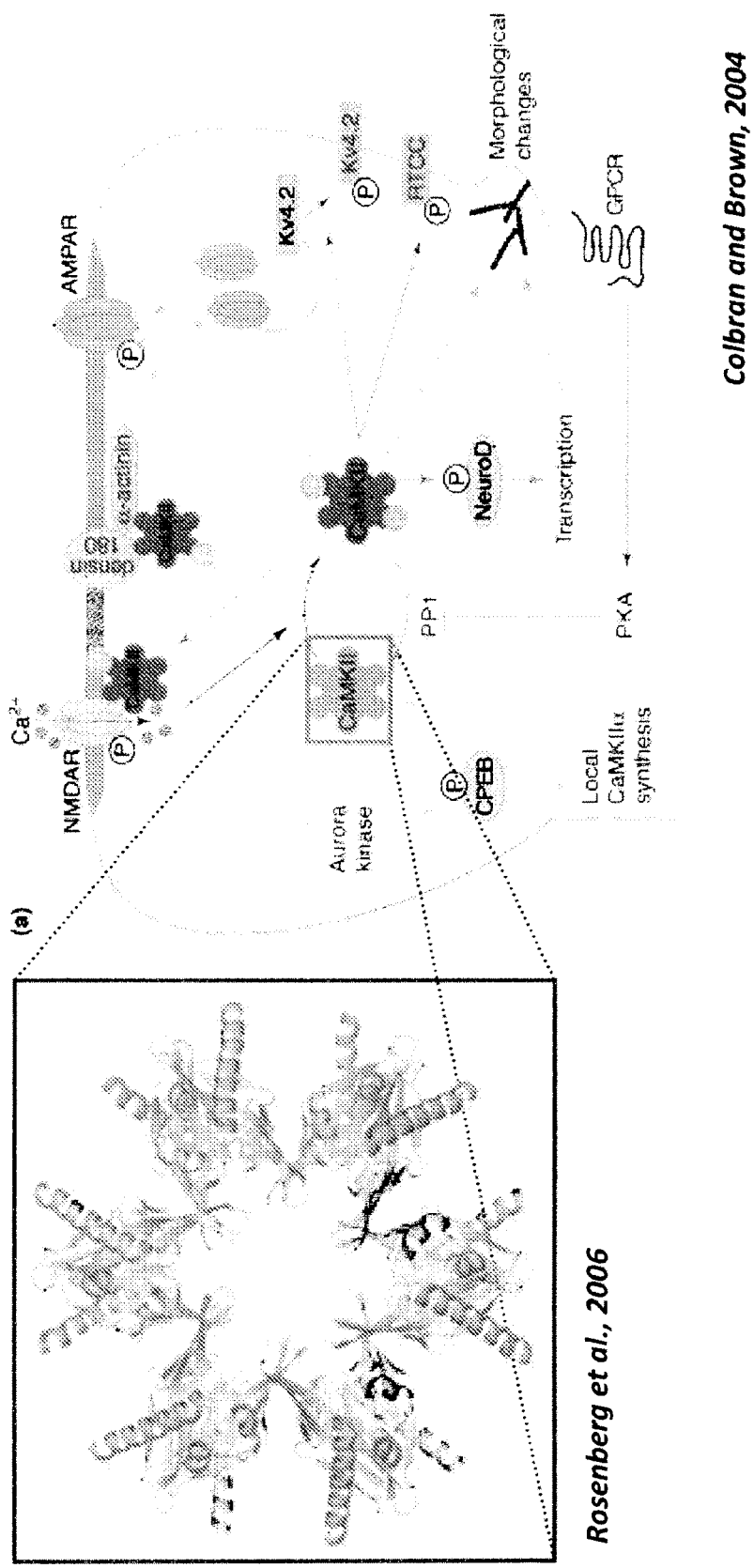
FIG. 12 shows the structure of yet another target endogenous protein, CAMKII alpha. The target domain by the intrabody is the multimerization domain of CAMKII alpha. This domain forms a hexagonal structure that serves as the scaffold for the CAMKII complex. This figure is adapted from Rosenberg O S et al. (2006) "Oligomerization states of the association domain and the holoenyzme of Ca2+/CaM kinase II," FEBS J. 273(4):682-94 and Colbran R J and Brown A M (2004) "Calcium/calmodulin-dependent protein kinase II and synaptic plasticity," Curr Opin Neurobiol. 14(3):318-27.

Yet another example is the multimerization domain of CAMKII alpha (FIG. 12). This domain forms a hexagonal structure that serves as the scaffold for the CAMKII complex.

Additionally, the list of polypeptide binders also includes 1) linear peptides (see for example (Ja, W. W., and Roberts, R. W. (2004) In vitro Selection of State-Specific Modulators of G Protein Signaling Using mRNA Display, Biochemistry 43:9265-9275)) 2) the lipocalin scaffold (Beste, G., et al. (1999) Small antibody-like protiens with prescribed ligand specificities derived from the lipocalin fold, Proc. Natl. Acad. Sci. USA 96:1898-1903), 3) the affibody scaffold (Hansson, M., et al. (1999) An in vitro selected binding protein (affibody) shows conformation-dependent recognition of the respiratory syncytial virus (RSV) G protein, Immunotechnology 4:237-252), 4) the DARPin scaffold (designed ankryin repeat proteins) (Kawe, M., et al. (2006) Isolation of intracellular proteinase inhibitors derived from designed ankyrin repeat proteins by genetic screening, Biol Chem 281:40252-40263).

Transcription factors and transcription regulatory elements are known in the art. In one aspect, the transcription factor comprises a Gal4 DNA binding domain and a Krab (A) domain. In this example the corresponding transcription regulatory element can be Gal4. In another aspect, the transcription regulatory element is one or more of a transcriptional control system, an inducible promoter, a transcriptional activator, e.g., VP16 transcriptional activator, a minimal promoter and transcriptional element that works in concert with the minimal promoter, e.g., a right-handed zinc finger DNA binding domain which optionally is fused to the T2A site. A non-limiting example of an inducible promoter is a domain from FRB which works in concert with FKRB and rapamycin (or a rapamycin analog, e.g., iRAP or a caged rapamycin analog) to control expression of a polynucleotide.

In addition to Gal4/Krab(A), there are a wide variety of transcription factors suitable for practicing the present technology. It is known that DNA binding domains can be used to create artificial fusion proteins that regulate transcription. The classic example of this is the yeast 2-hybrid system developed by Fields and Song (Fields, S., and Song, O.-k. (1989) A novel genetic system to detect protein-protein interactions, Nature 340:245-246). There are now many variants of the two-hybrid system, including the interaction trap (Gyuris, J. et al. (1993) Cdi1, a Human G1 and S Phase Protein Phosphatase That Associates with Cdk2, Cell 75:791-803), and several three-hybrid systems (see for example (Licitra, E., and Liu, J. O. (1996) A three-hybrid system for detecting ligand-protein receptor interactions, Proc. Natl. Acad. Sci. USA 93:12817; SenGupta, D. J., et al. (1996) A three-hybrid system to detect RNA-protein interactins in vivo, Proc. Natl. Acad. Sci. USA, 8496-8501)).

In the two-hybrid systems, a DNA binding domain (usually Gal4 or LexA) is fused to either a control protein (e.g., a transcription activation domain such as the Gal4 activating region), or to a bait protein that will then bind to a control protein. In the three hybrid systems, the bait binds to a second component (protein, drug, RNA) that then enables binding to the control protein.

It is also possible to block transcription by occlusion of the promoter. In this case, only a DNA binding domain is sufficient to serve as a transcription factor. In this approach, the DNA binding domain/DNA interaction overlaps or is close enough to the TATA box, that it prohibits proper formation of the transcription initiation complex. This type of regulation is seen in the bacterial Lac Operon (see for example (Monod, J., et al. (1965) On the Nature of Allosteric Transitions: A Plausible Model, J. Mol. Biol. 12:88-118; Straney, S. B., and Crothers, D. M. (1987) Lac Repressor is a Transient Gene-Activating Protein, Cell 51:699-707)). One example of a DNA-binding domain is a zinc finger that can be engineered to bind specific DNA binding sites (Rebar, E. J., Greisman, H. A., and Pabo, C. O. (1996) Phage Display Methods for Selecting Zinc Finger Proteins with Novel DNA-Binding Specificities, Methods in Enzymology 267:129-149; Rebar, E. J., and Pabo, C. O. (1994) Zinc Finger Phage: Affinity Selection of Fingers with New DNA-Binding Specificities, Science 263:671-673).

In some aspects, more than one transcription factor/transcription regulatory element is included in the polynucleotide to strengthen the inhibitory effect.

In one embodiment, the polynucleotide further includes a polynucleotide encoding a reporter such as a fluorescent protein.

There are two main families of fluorescent proteins in widespread use, those derived from green fluorescent protein (GFP), e.g., blue fluorescent protein (BFP), cyan fluorescent protein (CFP), yellow fluorescent protein (YFP) and those derived from the protein dsRed (e.g., mCherry) (Zhang, J., et al. (2002) Creating new fluorescent probes for cell biology, Nat Rev Mol Cell Biol 3:906-918).

These reporters can be used individually, or two proteins can be put together to make a FRET pair (Olson, C. A., et al. (2008) mRNA display selection of a high-affinity, modification-specific phospho-IkappaBalpha-binding fibronectin, ACS Chem. Biol. 3:480-485).

Additional examples of reporters include mCherry, dTomato, mPlum, mOrange, mCitrine, YPet, Cerulean CFP (Shaner, N. C., et al. (2005) A guide to choosing fluorescent proteins, Nat Methods 2:905-909).

Other commonly used optical reporters include enzymes capable of generating chemiluminescence such as luciferase (see for example (Dewet, J. R., et al. (1985) Cloning of Firefly Luciferase cDNA and the Expression of Active Luciferase in *Escherichia-Coli*, Proc. Natl. Acad. Sci. USA 82:7870-7873)) with an appropriate substrate (e.g., luciferin), or enzymes capable of generating colorimetric signals such as the b-galactosidase enzyme and the substrate X-gal (Berg, J. M., et al. (2007) Biochemistry, 6th ed., W.H. Freeman and Company, New York).

Still other exemplary reporters include fluorescent molecules such as SNAP, CLIP, ACP and MCP tags (NEB), which are not encoded in the protein of interest, but can be added later. The SNAP tag consists of a 20 kD mutant of the DNA repair protein O6-alkylguanine-DNA alkyltransferase. It reacts specifically with benzylguanine derivatives that can be conjugated to fluorescent molecules such as Alexa dyes.

Moreover, quantum dots, which are inorganic fluorescent molecules that are bright and resistant to bleaching (Alivisatos, A. P., et al. (2005) Quantum dots as cellular probes, Annu Rev Biomed Eng 7:55-76), can be conjugated to proteins such as Streptavidin, which can then interact with moieties on the intrabody such as the streptavidin binding peptide.

Proteins that can be labeled by the present technology can be an endogenous protein, including but not limited to, a transmembrane protein, a nucleic protein, a cytoplasmic protein, a secreted protein or an organelle protein. In a particular aspect, the endogenous protein is a transmembrane protein.

Methods for labeling an endogenous protein in a cell are also provided. The method, in one embodiment, comprises contacting the cell with a polynucleotide comprising (1) a nucleic acid sequence encoding a fusion polypeptide comprising (a) a binding moiety such as an antibody, an antigen binding fragment of an antibody or an antibody mimetic, (b) a reporter and (c) a transcription factor and (2) a transcription regulatory element operatively linked to the nucleic acid sequence, wherein the transcription regulatory element regulates the transcription of the binding moiety such as an antibody, the antigen binding fragment or the antibody mimetic and the transcription factor regulates the activity of the transcription regulatory element, and wherein the binding moiety such as an antibody, the antigen binding fragment or the antibody mimetic specifically recognizes the endogenous protein.

Compositions and Methods for Ablating an Endogenous Protein

The present disclosure also provides compositions for ablating, degrading, removing, or inhibiting an endogenous protein and provide for advantages over siRNA therapy. In one aspect, with use of the present compositions, the protein to be ablated is eliminated 1 hour and before there can be compensatory changes. Thus, one can better mimic the effect of blocking protein function with a drug and therefore is suitable for drug testing.

One can also eliminate proteins with specific post-translational modifications or that are in specific conformations that characterize the pathological protein, but are not present in the endogenous protein. Thus, can eliminate the pathological protein component, but not the wild-type protein. For example and without limitation, one can use to eliminate phosphorylated Tau that is part of neurofibrilllary tangles, Abeta in plaques, Alpha synuclein, huntingtin, prions etc.

In addition, the present compositions can be engineered to be inducible using a Rapamycin mediated association of FKBP and FRB domains. This will allow degradation to be done in a time-dependent manner. Using caged rapamycin degradation can be done in a light-activated manner that allows for control of time and position of degradation. Thus, one can eliminate specific proteins in cancer cells (e.g., proteins involved in resistance to chemotherapy) in a time and place specific manner.

Figure 2:
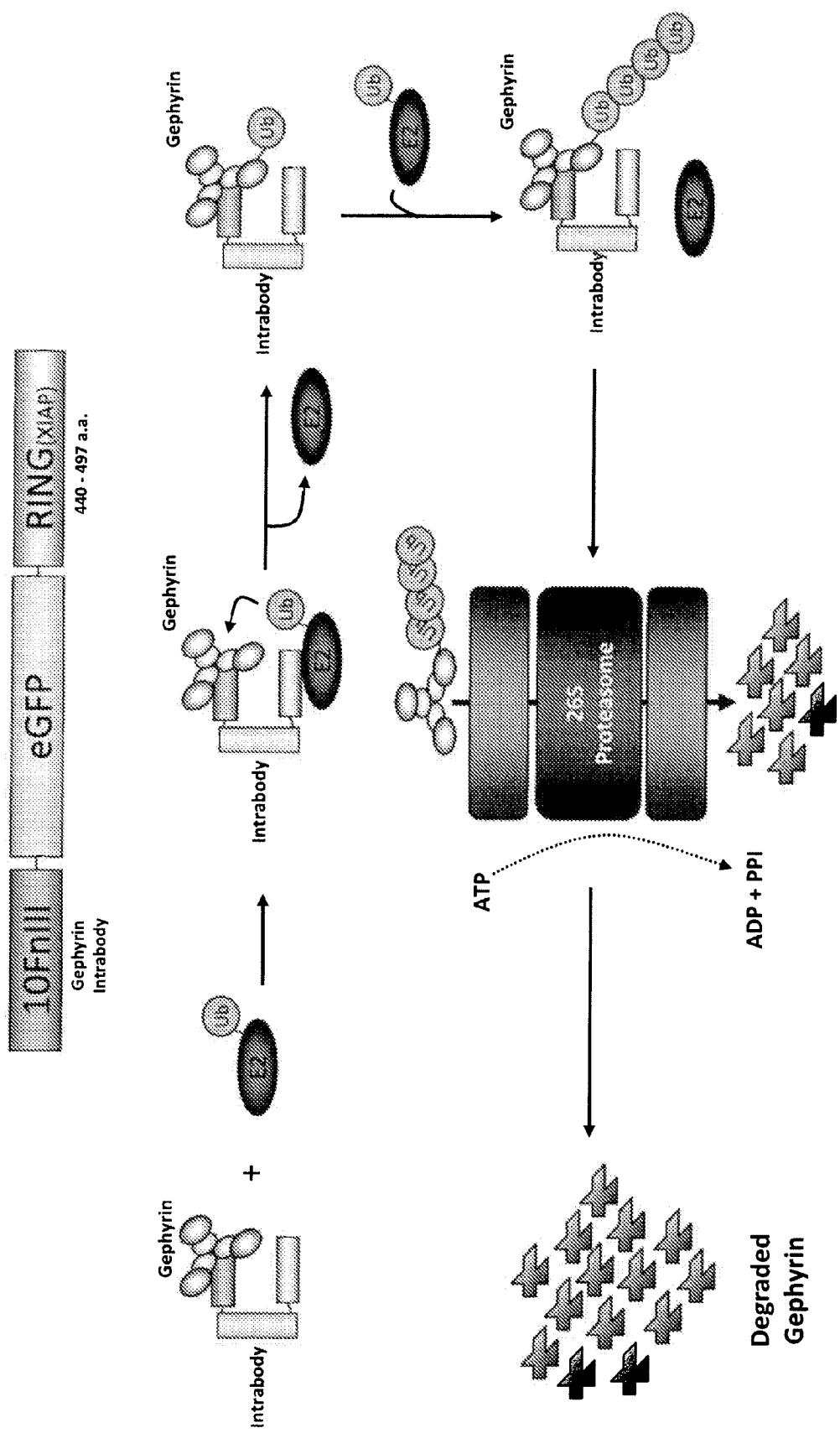
FIG. 2 illustrates an intrabody design for targeting and ablating a protein.

In one embodiment, provided is a binding moiety such as an antibody, an antigen binding fragment of an antibody, or an antibody mimetic is fused to a protein degradation signal (FIG. 2). Antibodies, antibody fragments and antibody mimetics are described above.

In one aspect, provided is a polynucleotide encoding a fusion polypeptide comprising a binding moiety and a protein degradation signal.

A "protein degradation signal" or "degron" refers to a peptide fragment that induces degradation of the protein that contains the fragment. Protein degradation can happen through any of the many known protein degradation pathways, including but not limited to, ubiquitination, lysomosal degradation or autophagy.

One example of protein degradation signal is a RING domain of X-linked inhibitor of aptosis protein (XIAP) (Tsai D E, et al. (1991) U1-snRNP-A protein selects a ten nucleotide consensus sequence from a degenerate RNA pool presented in various structural contexts. Nucleic Acids Research 19: 4931-4936), e.g., E3 ligase from XIAP (amino acids 440-497). XIAP induces protein ubiquitination. Additional examples are described in U.S. Patent Publ. No. 2004/0038358A1 (detailed in paragraphs [0021] through [0024]). Yet further examples include without limitation, a mammalian Double Minute 2 protein, e.g., a Human Double Minute 2 ("HDM2") or the mouse Double Minute 2 protein ("Mdm2").

Other ubiquitination domains include an E3 domain from Murine Double Minute "MDM2" (amino acids 403-458), a HECT domain e.g., from an E6 protein (Huibregtse, J. M., et al. (1995) A family of proteins structurally and functionally related to the E6-AP ubiquitin-protein ligase, Proc Natl Acad Sci USA 92:5249), from C20-WW-HECT (Dunn, R., et al. (2004) J. Cell Biol. 165:135-144). Also, the C2 domain of the Rsp5 ubiquitin ligase, which binds membrane phosphoinositides, directs ubiquitination of endosomal cargo), and is involved in degradation of membrane proteins.

Other RING domains include one in Der3/Hrd1 which is involved in endoplasmic reticulum-associated degradation (Bordallo, J., et al. (1998)), Der3p/Hrd1p is required for endoplasmic reticulum-associated degradation of misfolded lumenal and integral membrane proteins, Mol Biol Cell 9:209-222).

Moreover, RING-related domains include the B-box domain of the TRIM subfamily (Tao, H., et al. (2008) Structure of the MID1 tandem B-boxes reveals an interaction reminiscent of intermolecular ring heterodimers, Biochemistry 47:2450-2457) and the U-box domain (Aravind, L., and Koonin, E. V. (2000) The U box is a modified RING finger—a common domain in ubiquitination, Curr Biol 10:R132-134).

Signals that stimulate degradation via lysosomal pathways include, without limitation, KFERQ, a signal found in RNase family of proteins such as RNase A (Haigis, M. C., et al. (2002) KFERQ sequence in ribonuclease A-mediated cytotoxicity, J. Biol Chem 277:11576-11581).

Signals for induction of autophagy include, without limitation, Atg proteins, Atg12 and Atg8/LC3, which act like ubiquitin, and can initiate autophagic degradation (Yang, Z., and Klionsky, D. J. (2010) Mammalian autophagy: core molecular machinery and signaling regulation, Curr Opin Cell Biol 22:124-131).

The antibody-mimetic-degron approach described here should provide a significant improvement over siRNA because it targets protein directly and so ablation is not dependent on the inherent protein turnover rate. Rather, this approach enables direct targeting of a protein to the degradation machinery and should thus dramatically enhance the degradation of proteins relative to their inherent degradation rate. Because this method targets proteins (rather than mRNA), it should be possible to target proteins with specific conformations and post-translational modifications. For instance, this approach should enable targeting prion-like proteins such as Tau or Huntingtin in their mutant conformations, without affecting the native conformation of these proteins. A second example is that this approach should enable targeting mutant proteins whose signaling promotes tumor formation, such as oncogenic mutants of Ras, providing that mutant selective antibody-mimetic proteins can be found. Furthermore, this approach could be used to selectively target phosphorylated, acetylated, glycosylated, or other posttranslationally modified proteins for degradation.

Also provided is a polynucleotide comprising, consisting essentially of, or yet further consisting of, (1) a nucleic acid sequence encoding a fusion polypeptide comprising (a) a binding moiety and a protein degradation factor (b) a transcription factor and (2) a transcription regulatory element operatively linked to the nucleic acid sequence, wherein the transcription regulatory element regulates the transcription of the binding moiety and the transcription factor regulates the activity of the transcription regulatory element.

Further provided is a system for the expression of two or more polynucleotides, the system comprising a polynucleotide comprising a nucleic acid sequence encoding a fusion polypeptide comprising (a) a binding moiety and a protein degradation factor and (b) a transcription factor and a transcription regulatory element operatively linked to the nucleic acid sequence, wherein the transcription regulatory element regulates the transcription of the binding moiety and the transcription factor regulates the activity of the transcription regulatory element; a second nucleic acid sequence encoding a second fusion polypeptide comprising (a) a minimal promoter and (b) a transcription factor that mediates expression of the binding moiety and (c) a heterologous protein; wherein the transcription factor regulates the minimal promoter causing expression of the heterologous protein.

The polypeptides encoded by these polynucleotides are further provided herein.

Thus, the present disclosure also provides, in one embodiment, methods for inhibiting an activity of or degrading an endogenous protein in a cell, comprising contacting the cell with a polynucleotide comprising a nucleic acid sequence encoding a fusion polypeptide comprising (a) a binding moiety such as an antibody, an antigen binding fragment of an antibody or an antibody mimetic and (b) a protein degradation signal, wherein the antibody, the antigen binding fragment or the antibody mimetic specifically recognizes the endogenous protein.

The present disclosure, in some embodiments, provides a polypeptide encoded by a polynucleotide of any of the above embodiments, a DNA construct comprising a polynucleotide of any of the above embodiments, a composition comprising a polynucleotide of any of the above embodiments and a carrier, or a cell comprising any of the above.

In one aspect, the polypeptide or polynucleotide of the above embodiment is encapsulated. In another aspect, the polypeptide further comprises a cell penetrating peptide (CPP) that can be chemically or recombinantly linked to the polypeptide. In some aspects, a cell penetrating peptide can be a HIV-TAT peptide.

Treatment Methods and Screens

In some embodiments, the present disclosure provides methods for treating a condition or disease characterized by expression of an endogenous protein in a cell. The methods are applicable to animals, mammals or yet further human patients. For the purpose of illustration only, a mammal includes but is not limited to a human, a simian, a murine, a bovine, an equine, a porcine or an ovine.

Thus, methods for treating a disease characterized by expression of an endogenous protein in a cell are provided, comprising contacting the cell with a polynucleotide comprising a nucleic acid sequence encoding a fusion polypeptide comprising (a) a binding moiety such as an antibody, an antigen binding fragment of an antibody or an antibody mimetic and (b) a protein degradation signal, wherein the binding moiety specifically recognizes the endogenous protein.

Examples of such endogenous proteins, without limitation, include Tau, alpha-Synuclein, prion protein, Huntingtun, Nav1.7, CCR5, HER-2, EGFR, Estrogen receptor, an oncogene, or a drug resistant gene.

Many forms of cancer have aberrant expression of growth factor receptors on the surface. For example, HER2/neu positive breast cancer is characterized by massive overexpression of the HER2 receptor tyrosine kinase, up to 1.5 million copies per cell (Slamon, D. J., et al. (2001) Use of chemotherapy plus a monoclonal antibody against HER2 for metastatic breast cancer that overexpresses HER2, N Engl J Med 344:783-792). Therapeutic reagents that block homodimerization (such as the therapeutic antibody Herceptin) are effective clinically in treating this type of cancer.

It is noted that overexpression is not the only problem that could be addressed with this approach. Many oncogenes exist at same level as wt protein inside normal cells. There, the pathology of the mutant protein is due not to overexpression, but to aberrant function. For example, mutants of the Ras protein are present at the same level as the normal wt protein, but constitutively activate signaling of the MAP kinase cascade, thereby stimulating growth (Tabin, C. J., et al. (1982) Mechanism of activation of a human oncogene, Nature 300:143-149). Eliminating an aberrant protein could thus prove equally beneficial to eliminating overexpressed proteins.

Another example relates to HER2. HER2 signaling also mediates other types of tumors where it is not significantly overexpressed. Antibodies such as pertuzumab (Omnitarg) block heterodimeization with HER2 and other growth factor receptors (Baselga, et al. (2010) Phase II trial of pertuzumab and trastuzumab in patients with human epidermal growth factor receptor 2-positive metastatic breast cancer that progressed during prior trastuzumab therapy, J Clin Oncol 28:1138-1144).

Moreover, protein ablating can also be useful in treating HIV by, for example, ablating CCR5, or inducing stem cell differentiation by, for example, inhibiting histone deacytalase.

It is also known that the following neurological diseases are associated with overexpression and/or aberrant folding of neuronal proteins. Ablating intrabodies could, in theory, be used to reduce or eliminate the proteins that cause them. Such diseases include Parkinson's disease, Amyotrophic Lateral Sclerosis (Lou Gherig's disease), Creutzfeldt-Jakob disease, Huntington's, Alzheimer's, Dementia with Lewy Bodies, Pick's disease, Corticobasal degeneration, Progressive Supranuclear Palsy, Charcot Marie Tooth disease, Multiple system atrophy, or Chronic pain syndromes.

The compositions and methods are useful to determine to screen intrabodies to determine if the intrabody possesses the required in vivo efficacy. In one aspect, they are used to screen for stability and binding behavior in the cytoplasm of any protein. This application is suitable to binding proteins made with mRNA display, phage display etc.

In aspects where the binding moiety is to Gephyrin or PSD-95, the compositions and methods ase useful to monitor synaptic strength. Thus, they can be used for testing drugs or biologics to determine any effect on synaptic efficacy (i.e., memory loss). This also applies for diagnostics, for example, looking at Ca channels in pain sensitive neurons.

The system and compositions containing it are useful to regulate expression of heterologous proteins in a predictable and stable manner.

They also can be used for gene therapy because they can precisely and predictably regulate heterologous protein expression without requiring integration into the genome, the main stumbling block to gene therapy. For example, they can be used to treat cystic fibrosis, muscular dystrophy, expression of channel rhodopsin in specific subtypes of cells.

They also can be used for cell killing, e.g., one can express a toxin in a cell type that expresses a tumor marker or in a cell type that produces a specific antibody, e.g., plasma cells involved in autoimmunity.

Moreover, one can use the compositions and methods to activate stem cells or cause them to pursue a specific fate in vivo.

A therapeutic composition can include a polynucleotide, a polypeptide, a DNA construct, or a cell containing any of these. The formulation comprising the therapeutic composition is also provided. The formulation can further comprise one or more preservatives or stabilizers. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3. 0.4, 0.5, 0.9, 1.0%), 0.1-3% benzyl alcohol (e.g., 0.5, 0.9, 1.1, 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, and 1.0%).

The therapeutic composition can be administered as a composition. A "composition" typically intends a combination of the active agent and another carrier, e.g., compound or composition, inert (for example, a detectable agent or label) or active, such as an adjuvant, diluent, binder, stabilizer, buffers, salts, lipophilic solvents, preservative, adjuvant or the like and include pharmaceutically acceptable carriers. Carriers also include pharmaceutical excipients and additives proteins, peptides, amino acids, lipids, and carbohydrates (e.g., sugars, including monosaccharides, di-, tri-, tetra-oligosaccharides, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/ antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this invention, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

The term carrier further includes a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Additional carriers include polymeric excipients/additives such as polyvinylpyrrolidones, ficolls (a polymeric sugar), dextrates (e.g., cyclodextrins, such as 2-hydroxypropyl-.quadrature.-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives and any of the above noted carriers with the additional proviso that they be acceptable for use in vivo. For examples of carriers, stabilizers and adjuvants, see Martin REMINGTON'S PHARM. SCI., 15th Ed. (Mack Publ. Co., Easton (1975) and Williams & Williams, (1995), and in the "PHYSICIAN'S DESK REFERENCE", $52^{nd}$ ed., Medical Economics, Montvale, N.J. (1998).

The invention provides an article of manufacture, comprising packaging material and at least one vial comprising a solution of the chemotherapy as described herein and/or or at least one antibody or its biological equivalent with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further comprises an article of manufacture, comprising packaging material, a first vial comprising the chemotherapy and/or at least one lyophilized antibody or its biological equivalent and a second vial comprising an aqueous diluent of prescribed buffer or preservative, wherein said packaging material comprises a label that instructs a patient to reconstitute the therapeutic in the aqueous diluent to form a solution that can be held over a period of twenty-four hours or greater.

The agents identified herein as effective for their intended purpose can be administered to subjects or individuals identified by the methods herein as suitable for the therapy. Therapeutic amounts can be empirically determined and will vary with the pathology being treated, the subject being treated and the efficacy and toxicity of the agent.

Also provided is a medicament or a therapy comprising an effective amount of a chemotherapeutic as described herein for treatment of a human cancer patient having high or low gene expression or the polymorphism of the gene of interest as identified in the experimental examples.

Methods of administering pharmaceutical compositions are well known to those of ordinary skill in the art and include, but are not limited to, oral, microinjection, intravenous or parenteral administration. The compositions are intended for topical, oral, or local administration as well as intravenously, subcutaneously, or intramuscularly. Administration can be effected continuously or intermittently throughout the course of the treatment. Methods of determining the most effective means and dosage of administration are well known to those of skill in the art and will vary with the cancer being treated and the patient. and the subject being treated. Single or multiple administrations can be carried out with the dose level and pattern being selected by the treating physician.

Vectors Suitable for Delivery to Humans

In one aspect, the disclosure features gene therapy methods of delivering a polynucleotide to a patient. Gene therapy, including the use of viral vectors as described herein, seeks to transfer new genetic material (e.g., polynucleotides encoding proteins or a biologically active fragment thereof) to the cells of a patient with resulting therapeutic benefit to the patient.

A "gene delivery vehicle" is defined as any molecule that can carry inserted polynucleotides into a host cell. Examples of gene delivery vehicles are liposomes, micelles biocompatible polymers, including natural polymers and synthetic polymers; lipoproteins; polypeptides; polysaccharides; lipopolysaccharides; artificial viral envelopes; metal particles; and bacteria, or viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

A polynucleotide of this invention can be delivered to a cell or tissue using a gene delivery vehicle. "Gene delivery," "gene transfer," "transducing," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein.

A "plasmid" is an extra-chromosomal DNA molecule separate from the chromosomal DNA which is capable of replicating independently of the chromosomal DNA. In many cases, it is circular and double-stranded. Plasmids provide a mechanism for horizontal gene transfer within a population of microbes and typically provide a selective advantage under a given environmental state. Plasmids may carry genes that provide resistance to naturally occurring antibiotics in a competitive environmental niche, or alternatively the proteins produced may act as toxins under similar circumstances.

"Plasmids" used in genetic engineering are called "plasmic vectors". Many plasmids are commercially available for such uses. The gene to be replicated is inserted into copies of a plasmid containing genes that make cells resistant to particular antibiotics and a multiple cloning site (MCS, or polylinker), which is a short region containing several commonly used restriction sites allowing the easy insertion of DNA fragments at this location. Another major use of plasmids is to make large amounts of proteins. In this case, researchers grow bacteria containing a plasmid harboring the gene of interest. Just as the bacteria produces proteins to confer its antibiotic resistance, it can also be induced to produce large amounts of proteins from the inserted gene. This is a cheap and easy way of mass-producing a gene or the protein it then codes for.

A "viral vector" is defined as a recombinantly produced virus or viral particle that comprises a polynucleotide to be delivered into a host cell, either in vivo, ex vivo or in vitro. Examples of viral vectors include retroviral vectors, adenovirus vectors, adeno-associated virus vectors, alphavirus vectors and the like. Infectious tobacco mosaic virus (TMV)-based vectors can be used to manufacturer proteins and have been reported to express Griffithsin in tobacco leaves (O'Keefe et al. (2009) Proc. Nat. Acad. Sci. USA 106(15):6099-6104). Alphavirus vectors, such as Semliki Forest virus-based vectors and Sindbis virus-based vectors, have also been developed for use in gene therapy and immunotherapy. See, Schlesinger & Dubensky (1999) Curr. Opin. Biotechnol. 5:434-439 and Ying et al. (1999) Nat. Med. 5(7):823-827. In aspects where gene transfer is mediated by a retroviral vector, a vector construct refers to the polynucleotide comprising the retroviral genome or part thereof, and a therapeutic gene.

As used herein, "retroviral mediated gene transfer" or "retroviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. As used herein, retroviral vector refers to a viral particle capable of introducing exogenous nucleic acid into a cell through a viral or viral-like entry mechanism.

Retroviruses carry their genetic information in the form of RNA; however, once the virus infects a cell, the RNA is reverse-transcribed into the DNA form which integrates into the genomic DNA of the infected cell. The integrated DNA form is called a provirus.

In aspects where gene transfer is mediated by a DNA viral vector, such as an adenovirus (Ad) or adeno-associated virus (AAV), a vector construct refers to the polynucleotide comprising the viral genome or part thereof, and a transgene. Adenoviruses (Ads) are a relatively well characterized, homogenous group of viruses, including over 50 serotypes. See, e.g., International PCT Application No. WO 95/27071. Ads do not require integration into the host cell genome. Recombinant Ad derived vectors, particularly those that reduce the potential for recombination and generation of wild-type virus, have also been constructed. See, International PCT Application Nos. WO 95/00655 and WO 95/11984. Wild-type AAV has high infectivity and specificity integrating into the host cell's genome. See, Hermonat & Muzyczka (1984) Proc. Natl. Acad. Sci. USA 81:6466-6470 and Lebkowski et al. (1988) Mol. Cell. Biol. 8:3988-3996.

Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

Gene delivery vehicles also include DNA/liposome complexes, micelles and targeted viral protein-DNA complexes. Liposomes that also comprise a targeting antibody or fragment thereof can be used in the methods of this invention. In addition to the delivery of polynucleotides to a cell or cell population, direct introduction of the proteins described herein to the cell or cell population can be done by the non-limiting technique of protein transfection, alternatively culturing conditions that can enhance the expression and/or promote the activity of the proteins of this invention are other non-limiting techniques.

For in vivo gene therapy, expression vectors encoding the gene of interest is administered directly to the patient. The vectors are taken up by the target cells (e.g., neurons or pluripotent stem cells) and the gene expressed. Recent reviews discussing methods and compositions for use in gene therapy include Eck et al., in Goodman & Gilman's The Pharmacological Basis of Therapeutics, Ninth Edition, Hardman et al., eds., McGray-Hill, New York, 1996, Chapter 5, pp. 77-101; Wilson, Clin. Exp. Immunol. 107 (Suppl. 1):31-32, 1997; Wivel et al., Hematology/Oncology Clinics of North America, Gene Therapy, S. L. Eck, ed., 12(3):483-501, 1998; Romano et al., Stem Cells, 18:19-39, 2000, and the references cited therein. U.S. Pat. No. 6,080,728 also provides a discussion of a wide variety of gene delivery methods and compositions.

Adenoviruses are able to transfect a wide variety of cell types, including non-dividing cells. There are more than 50 serotypes of adenoviruses that are known in the art, but the most commonly used serotypes for gene therapy are type 2 and type 5. Typically, these viruses are replication-defective; and genetically-modified to prevent unintended spread of the virus. This is normally achieved through the deletion of the E1 region, deletion of the E1 region along with deletion of either the E2 or E4 region, or deletion of the entire adenovirus genome except the cis-acting inverted terminal repeats and a packaging signal (Gardlik et al., (2205) Med Sci Monit. 11: RA110-121).

Retroviruses are also useful as gene therapy vectors and usually (with the exception of lentiviruses) are not capable of transfecting non-dividing cells. Accordingly, any appropriate type of retrovirus that is known in the art may be used, including, but not limited to, HIV, SIV, FIV, EIAV, and Moloney Murine Leukaemia Virus (MoMLV). Typically, therapeutically useful retroviruses including deletions of the gag, pol, or env genes.

In another aspect, the invention features the methods of gene therapy that utilize a lentivirus vectors to express Toso, or other proteins in a patient. Lentiviruses are a type of retroviruses with the ability to infect both proliferating and quiescent cells. An exemplary lentivirus vector for use in gene therapy is the HIV-1 lentivirus. Previously constructed genetic modifications of lentiviruses include the deletion of all protein encoding genes except those of the gag, pol, and rev genes (Moreau-Gaudry et al., Blood. 98: 2664-2672, 2001).

Adeno-associated virus (AAV) vectors can achieve latent infection of a broad range of cell types, exhibiting the desired characteristic of persistent expression of a therapeutic gene in a patient. The invention includes the use of any appropriate type of adeno-associated virus known in the art including, but not limited to AAV1, AAV2, AAV3, AAV4, AAV5, and AAV6 (Lee et al., (2005) Biochem J. 387:1-15; U.S. Patent Publication 2006/0204519).

Herpes simplex virus (HSV) replicates in epithelial cells, but is able to stay in a latent state in non-dividing cells such as the midbrain dopaminergic neurons. The gene of interest may be inserted into the LAT region of HSV, which is expressed during latency. Other viruses that have been shown to be useful in gene therapy include parainfluenza viruses, poxviruses, and alphaviruses, including Semliki forest virus, Sinbis virus, and Venezuelan equine encephalitis virus (Kennedy, (1997) Brain. 120:1245-1259).

Exemplary non-viral vectors for delivering nucleic acid include naked DNA; DNA complexed with cationic lipids, alone or in combination with cationic polymers; anionic and cationic liposomes; DNA-protein complexes and particles comprising DNA condensed with cationic polymers such as heterogeneous polylysine, defined-length oligopeptides, and polyethylene imine, in some cases contained in liposomes; and the use of ternary complexes comprising a virus and polylysine-DNA. In vivo DNA-mediated gene transfer into a variety of different target sites has been studied extensively. Naked DNA may be administered using an injection, a gene gun, or electroporation. Naked DNA can provide long-term expression in muscle. See Wolff, et al. (1990) Human Mol. Genet., 1:363-369; Wolff, et al., (1992) Science, 247:1465-1468. DNA-mediated gene transfer has also been characterized in liver, heart, lung, brain and endothelial cells. See Zhu, et al., (1993) Science, 261:209-211; Nabel, et al. (1989) Science 244:1342-1344. DNA for gene transfer also may be used in association with various cationic lipids, polycations and other conjugating substances. See Przybylska et al. (2004) J. Gene Med. 6:85-92; Svahn, et al. (2004) J. Gene Med. 6:S36-S44.

Methods of gene therapy using cationic liposomes are also well known in the art. Exemplary cationic liposomes for use in this invention are DOTMA, DOPE, DOSPA, DOTAP, DC-Chol, Lipid GL-67™, and EDMPC. These liposomes may be used in vivo or ex vivo to encapsulate a vector for delivery into target cells (e.g., neurons or pluripotent stem cells).

Typically, vectors made in accordance with the principles of this disclosure will contain regulatory elements that will cause constitutive expression of the coding sequence. Desirably, neuron-specific regulatory elements such as neuron-specific promoters are used in order to limit or eliminate ectopic gene expression in the event that the vector is incorporated into cells outside of the target region. Several regulatory elements are well known in the art to direct neuronal specific gene expression including, for example, the neural-specific enolase (NSE), and synapsin-1 promoters (Morelli et al. (1999) J. Gen. Virol. 80:571-583).

Methods of Delivering a Polypeptide

Methods of delivering a polypeptide, such as one that includes an intrabody for ablating an endogenous protein, to a cell, are generally known in the art. For example, the polypeptide can be delivered to a eukaryotic cell by a type III sercreation machine. See, e.g., Galan and Wolf-Watz (2006) Nature 444:567-73. Biologically active and full length protein, for another example, can also be delivered into a cell using cell penetraint peptides (CPP) as delivery vehicles. The trans-activating transcriptional activator (TAT) from human immunodeficiency virus 1 (HIV-1) is such a CPP, which is able to deliver different proteins, such as horseradish peroxidase and RNase A across cell membrane into the cytoplasm in different cell lines. Wadia et al. (2004) Nat. Med 10:310-15. Accordingly, in one aspect, the polypeptide can be delivered to a cell using TAT as a vehicle.

Liposomes, microparticles and nanoparticles are also known to be able to facilitate delivery of proteins or peptides to a cell by encapsulating the peptides (reviewed in Tan et al. (2010) Peptides 31(1):184-93). The liposomes, microparticles or nanoparticles can also comprise a targeting antibody or fragment thereof can be used in the methods of this invention. To enhance delivery to a cell, the proteins can be conjugated to antibodies or binding fragments thereof which bind cell surface antigens, e.g., a cell surface marker found on progentior cells.

In another aspect, non-covalent method which forms CPP/protein complexes has also been developed to address the limitations in covalent method such as chemical modification before crosslinking and denaturation of proteins before delivery. For example, a short amphipathic peptide carrier, Pep-1 and protein complexes have proven effective for delivery. It was shown that Pep-1 could facilitate rapid cellular uptake of various peptides, proteins and even full-length antibodies with high efficiency and less toxicity. Cheng et al. (2001) Nat. Biotechnol. 19:1173-6.

Proteins can be synthesized for delivery. Nucleic acids that encode a protein or fragment thereof may be introduced into various cell types or cell-free systems for expression, thereby allowing purification of the proteins, for large-scale production and patient therapy.

Eukaryotic and prokaryotic expression systems may be generated in which a gene sequence is introduced into a plasmid or other vector, which is then used to transform living cells. Constructs in which the cDNA contains the entire open reading frame inserted in the correct orientation into an expression plasmid may be used for protein expression. Prokaryotic and eukaryotic expression systems allow for the protein to be recovered, if desired, as fusion proteins or further containing a label useful for detection and/or purification of the protein. Typical expression vectors contain regulatory elements that direct the synthesis of large amounts of mRNA corresponding to the inserted nucleic acid in the plasmid-bearing cells. They may also include a eukaryotic or prokaryotic origin of replication sequence allowing for their autonomous replication within the host organism, sequences that encode genetic traits that allow vector-containing cells to be selected for in the presence of otherwise toxic drugs, and sequences that increase the efficiency with which the synthesized mRNA is translated. Stable long-term vectors may be maintained as freely replicating entities by using regulatory elements of, for example, viruses (e.g., the OriP sequences from the Epstein Barr Virus genome). Cell lines may also be produced that have integrated the vector into the genomic DNA, and in this manner the gene product is produced on a continuous basis.

Expression of foreign sequences in bacteria, such as *Escherichia coli*, requires the insertion of the nucleic acid sequence into a bacterial expression vector. Such plasmid vectors contain several elements required for the propagation of the plasmid in bacteria, and for expression of the DNA inserted into the plasmid. Propagation of only plasmid-bearing bacteria is achieved by introducing, into the plasmid, selectable marker-encoding sequences that allow plasmid-bearing bacteria to grow in the presence of otherwise toxic drugs. The plasmid also contains a transcriptional promoter capable of producing large amounts of mRNA from the cloned gene. Such promoters may be (but are not necessarily) inducible promoters that initiate transcription upon induction. The plasmid also preferably contains a polylinker to simplify insertion of the gene in the correct orientation within the vector.

Stable or transient cell line clones of mammalian cells can also be used to express a protein. Appropriate cell lines include, for example, COS, HEK293T, CHO, or NIH cell lines.

Once the appropriate expression vectors containing a gene, fragment, fusion, or mutant are constructed, they are introduced into an appropriate host cell by transformation techniques, such as, but not limited to, calcium phosphate transfection, DEAE-dextran transfection, electroporation, microinjection, protoplast fusion, or liposome-mediated transfection. The host cells that are transfected with the vectors of this invention may include (but are not limited to) *E. coli* or other bacteria, yeast, fungi, insect cells (using, for example, baculoviral vectors for expression in SF9 insect cells), or cells derived from mice, humans, or other animals (e.g., mammals). In vitro expression of a protein, fusion, polypeptide fragment, or mutant encoded by cloned DNA may also be used. Those skilled in the art of molecular biology will understand that a wide variety of expression systems and purification systems may be used to produce recombinant proteins and fragments thereof.

Once a recombinant protein is expressed, it can be isolated from cell lysates using protein purification techniques such as affinity chromatography. Once isolated, the recombinant protein can, if desired, be purified further by e.g., by high performance liquid chromatography (HPLC; e.g., see Fisher, Laboratory Techniques In Biochemistry And Molecular Biology, Work and Burdon, Eds., Elsevier, 1980).

Methods for Preparing and Testing Antibody Mimetics

A method is provided to test whether a binding moiety, such as an intrabody, or any other antibody, antibody fragment or antibody mimetic, in an intracellular environment, has the capacity to (1) bind to the target protein, (2) fold correctly intracellulary, (3) not aggregate, and (4) not bind to non-target proteins.

In general antibodies, fragment or mimetics are generated against target molecules in either an in vitro environment (e.g., mRNA display, phage display, ribosome display) or in an in vivo environment that is unlike the cytoplasm of mammalian cells (e.g., bacteria display, yeast display). Thus, often these molecules do not behave well when they are expressed in mammalian cells. To overcome this problem a screen is developed to assess the ability of individual intrabodies to bind specifically and efficiently to their targets in an intracellular environment.

It is understood that for a protein can target a selected place in a cell if (1) the protein binds at high affinity to a target molecule that is localized in that place and (2) the protein is folded correctly initially and it morphology and function is maintained in the intracellular environment.

To this end, the present disclosure provides a composition or kit that comprises (1) a first polynucleotide encoding a fusion polypeptide comprising a binding moiety such as an antibody, an antigen binding fragment of an antibody or an antibody mimetic and a reporter and (2) a second polynucleotide encoding a fusion polypeptide comprising a target peptide sequence and a cell localization domain, wherein the binding moiety mimetic specifically recognizes the target peptide sequence.

A cell localization domain is a peptide sequence that localizes the protein that includes the sequence at a specific intracellular location, such as the membrane of a cell organelle, including but not limited to Golgi apparatus, endoplasmic reticulum, lysosome, mitochondria, plasma membrane, or apical or basolateral domain of an epithelial cell.

Figure 3:
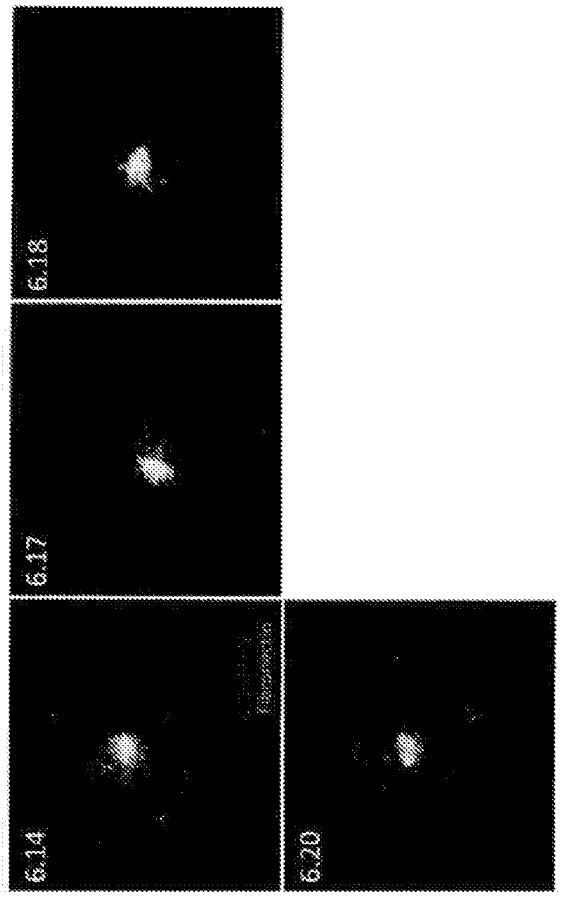
FIG. 3 demonstrates that the specificity and binding efficiency of an intrabody can be tested by colocalizing it with the target that is specifically localized in a cell. ("Winners") Fibronectins 6.9, 6.6, 6.7, 6.12, 6.16, 6.19, 6.21, and 6.22 (light gray), which colocalized with Golgi-targeted Gephyrin (dark gray) indicating that they worked well as intrabodies. ("Losers") Fibronectins 6.14, 6.17, 6.18, 6.20 localized somewhat nonspecifically indicating that they did not perform well as intrabodies. ("Controls") Fibronectins 6.6, 6.7, 6.9, and 6.18 colocalized nonspecifically when coexpressed with the Golgi-targeting sequence alone indicating that targeting to the Golgi did not occur in the absence of target protein.
Figure 3:
Figure 3:
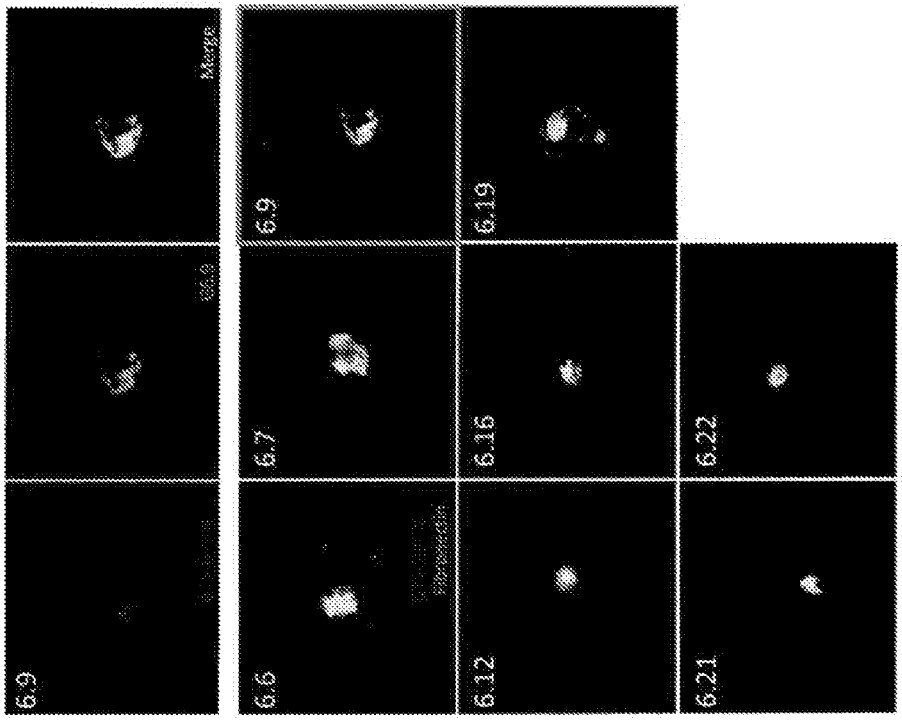

After both polynucleotide are introduced into a cell, the localization patterns of the binding moiety and the target protein are then compared. If they match and both proteins appeared to be colocalized in the correct region, and there was no aggregation or significant background, then it shows that the antibody binds at high affinity and specificity in an intracellular environment (FIG. 3).

It would be readily appreciated by the skilled artisan that any subcellular target could substitute for Golgi Apparatus, such as, but not limited to, Endoplasmic reticulum, lysosomes, mitochondria, plasma membrane, apical or basolateral domain of epithelial cells, etc.)

EXPERIMENTAL EXAMPLES

Example 1—Selection of Targeting Intrabodies

Figure 7:
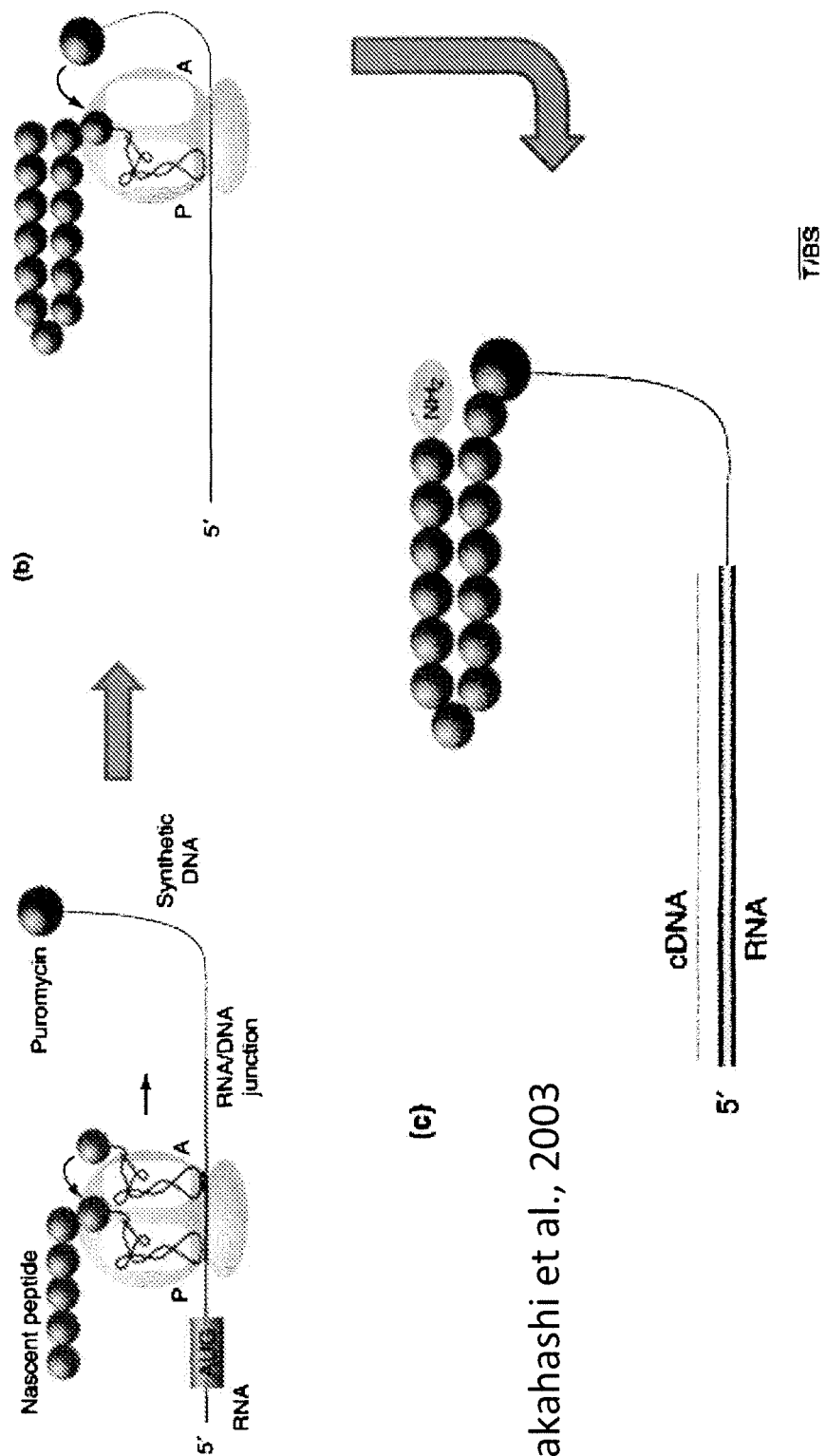
FIGS. 7A-C illustrate a method to generate a recombinant aptamer capable of binding to endogenous proteins in living cells (adapted from Takahashi T T et al. (2003) "mRNA display: ligand discovery, interaction analysis and beyond," Trends Biochem Sci., March; 28(3):159-65).
Figure 8:
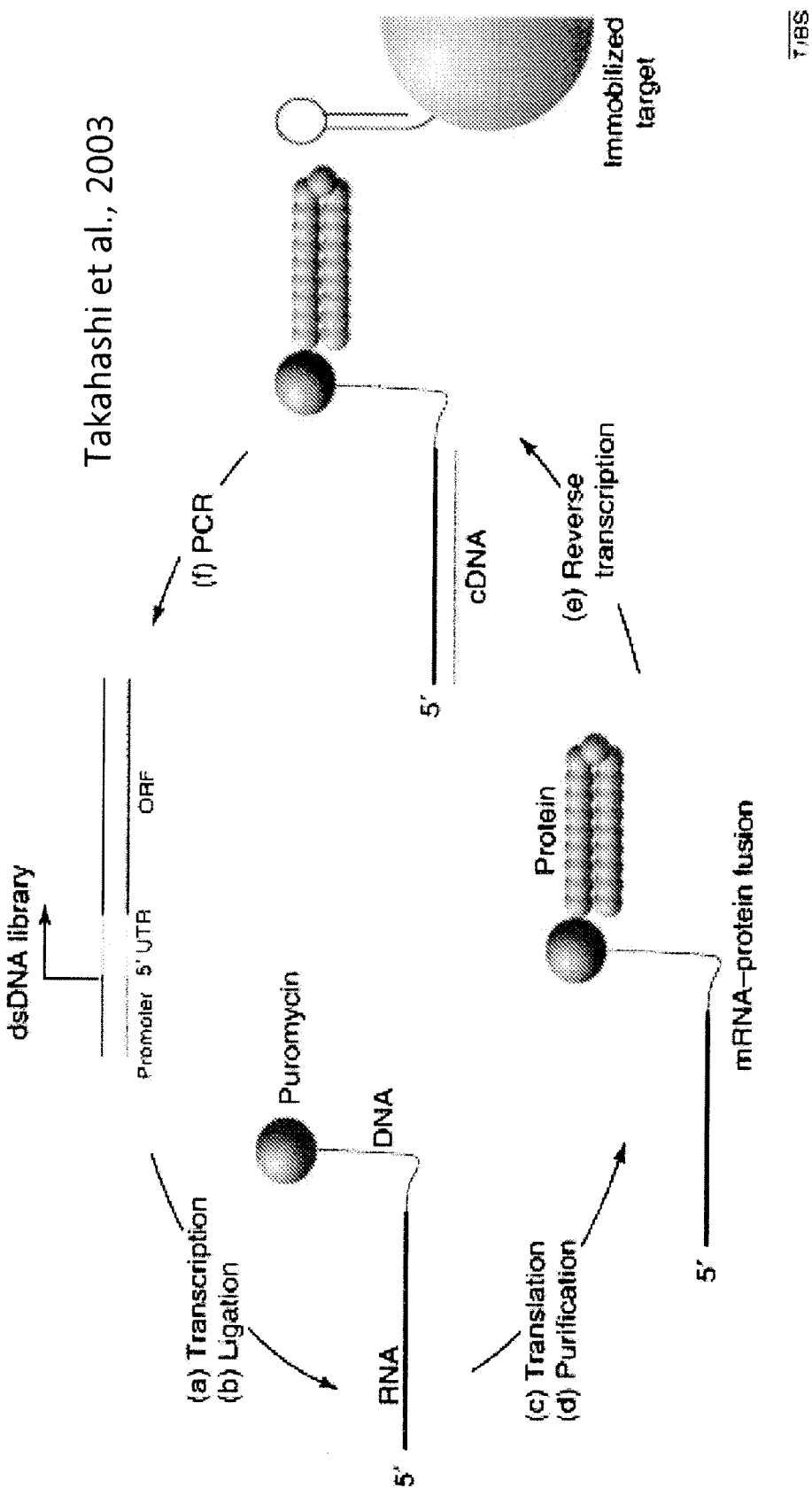
FIG. 8 illustrates fusion mRNA selection, which starts with a library of $10^{13}$ distinct DNA oligos, following by transcription, adding puromycin, translation and selection against antigen. Afterwards, antigen is used to purify tight binders, which are amplified to enrich the library for tight binders. After a few repeats, when selection has converged, then DNA is PCR'ed out (adapted from Takahashi T T et al. (2003), supra).

Intrabodies were selected from a double-stranded DNA library encoding a protein based on the 10fnIII scaffold with random substitutions in 17 residues in the BC and FG loops (Koide A, Bailey C W, Huang X, Koide S (1998) The fibronectin type III domain as a scaffold for novel binding proteins. J Mol Biol 284:1141-1151). See illustrations in FIGS. 7 and 8. This library had a diversity of $\sim 10^{13}$ and copy number of ~5.

For each round of selection the library was PCR amplified to a concentration of ~10 ng/μl, as assayed by agarose gel electrophoresis using a small mass analytical DNA ladder. 100 nM of library DNA was then transcribed in vitro by T7 RNA polymerase for 2-4 hours at 37° C. The transcription reaction was stopped by addition of 50 mM EDTA and then phenol/chloroform extracted, desalted using a CENTRI-SEP™ (Applied Biosystems) column, and finally ethanol precipitated.

Afterward library RNA was resuspended in ddH$_2$O and its concentration calculated based on its A$_{260}$ absorbance using a NANODROP™ (Thermo Scientific) spectrophotometer. Libray RNA was then ligated to Puromycin (10 μM), via a single-stranded DNA splint oligo (15 μM), using T4 DNA Ligase at RT for 1 hour. Puromycin ligated library RNA was then phenol/chloroform extracted and ethanol precipitated before being purified by Urea-PAGE electrophoresis and collected by electroelution.

Following Urea-PAGE purification and electroelution, Puromycin ligated library RNA was once more ethanol precipitated and then resuspended in ddH$_2$O. Puromycin ligated library RNA concentration was then calculated spectrophotometrically by NANODROP™ and diluted to a 5 μM working concentration. 40-200 pmoles of ligated RNA was subsequently in vitro translated using a rabbit reticulocyte lysate system, nuclear treated (Promega) for 1 hour at 30° C. Addition of a 2.77× stock solution containing 7:2 (2.5M KCl:1M MgCl$_2$) facilitated covalent bond formation between Puromycin-ligated RNA and the C-terminus of nascently translated protein still attached to the Ribosome. These protein-Puromycin-RNA fusions were then purified by incubation of the reticulocyte in dT cellulose (0.08 mg/µl of reticulocyte; GE Healthcare Lifesciences) with dT cellulose buffer containing EDTA (100 mM Tris-HCl, pH 8.0; 1M NaCl; 10 mM EDTA; 0.2% Triton X-100) for 1 hour at 4° C.

Thereafter, protein-RNA fusions were washed three times with dT Buffer containing EDTA and twice with dT Buffer lacking EDTA. Protein-RNA fusions were then eluted from dT celluose with ddH$_2$O, and the eluate desalted using a CENTRI-SEP™ column. Lastly, a complementary DNA (cDNA)-RNA duplex was generated from the protein-RNA fusions using a reverse-transcriptase-mediated reaction and a reverse (DNA) oligo that anneals to a conserved sequence at the 3'-5' end of the Puromycin-ligated RNA.

Target protein was prepared by biotinylating it on the N-terminus or C-terminus using a biotin acceptor tag. The free biotinylated target was then incubated with agarose or polyacrylamide beads conjugated with Strepavidin or NEUTRAVIDIN® for one hour at 4° C. Afterward target bound to beads was washed with a blocking solution containing $TBS_{tween(0.2\%)}$, BSA (0.5 mg/ml), DTT (1 mM), FBS (10%), sheared samon sperm DNA (0.1 mg/ml), and Biotin (0.2 mM). Target bound to beads was then exposed to the library for 1 hour at room temperature in blocking solution.

For rounds of selection 1-3 saturating levels of target were bound to beads, whereas in all subsequent rounds of selection considerably less target was bound to the beads, with target concentrations usually ranging from 100-1000 pmoles. Rounds of selection continue until a pool of high affinity binders has been selected and/or library convergence has been reached. Library convergence was indicated by percent binding of protein-mRNA hybrids to target as determined by counts from $^{35S}$Met radiolabeling and by a reduction in the number of PCR cycles required to amplify the selected cDNAs, and was confirmed by sequencing a series of clones from the amplified library. Clones were then subcloned into expression plasmids in such a way that they form a gene encoding a fusion protein consisting of the intrabody fused to a fluorescent protein.

To test in vivo efficacy of the intrabodies, individual intrabody clones were coexpressed in COS cells with a construct encoding the target protein that was fused with a peptide signal that mediated targeting to the Golgi apparatus (Corse E, Machamer C E (2002) The cytoplasmic tail of infectious bronchitis virus E protein directs Golgi targeting. J Virol 76:1273-1284). Fluorescent protein fused intrabodies that showed colocalization with Golgi-localized target in COS cells were then tested in cortical neurons in dissociated culture. The expression pattern of the expressed intrabody was then compared with that of the endogenous target protein to determine whether the intrabody effectively labels the target protein (see Example 2).

Example 2—Determination of Specificity and Efficiency of Intrabodies

This examples shows how an intrabody, or any other antibody, antibody fragment or antibody mimetic, is tested for its capability, in an intracellular environment, to (1) bind to the target protein, (2) fold correctly intracellularly, (3) not aggregate, and (4) not bind to non-target proteins.

Following mRNA display selection, Fibronectin clones from late rounds that had been selected to bind with high affinity to a target molecule were cloned into an expression plasmid that has been engineered so that a GFP tag was fused to the fibronectin upon expression. A second construct was made encoding the target domain fused with a short peptide that mediates localization to the Golgi apparatus (Andersson, A. M., et al. (1997) A retention signal necessary and sufficient for Golgi localization maps to the cytoplasmic tail of a Bunyaviridae (Uukuniemi virus) membrane glycoprotein, J Virol 71: 4717-4727).

The two plasmids above were cotransfected into COS cells (or any other transfectable cell line, including, but not limited to, HEK, 3T3 or CHO) in such quantities that the proteins were expressed at roughly equal levels. Furthermore, the target construct must be expressed in sufficient quantity that it could be easily detected, but at a low enough level that it was efficiently targeted to the Golgi apparatus. It is noted that, in practice, this is a wide range and achieving appropriate expression levels can be achieved with ordinary techniques known in the art. Following expression for 14 hours the proteins could be observed directly if two different fluorescent proteins (e.g., mCherry and GFP) were attached to the intrabody and Golgi-localized target protein or the cells could be fixed and stained with antibodies or other labeling molecules.

The localization patterns of the two proteins were then compared. If they matched and both proteins appeared to be colocalized in the correct region, the Golgi (a small perinuclear structure that often appears reticular) in this case, and there was no aggregation or significant background, then it's concluded that the intrabody bound at high affinity and specificity in an intracellular environment.

As a control it is necessary to coexpress the intrabody with just the localization signal and without the target protein (e.g., Gephyrin G domain). If the intrabody does not localize correctly (to the Golgi in this case), one can assume that any targeting seen in the first assay was, in fact, due to binding of the intrabody to the target protein. Examples of clones that behaved well and those that did not are shown in FIG. 3.

Figure 13:
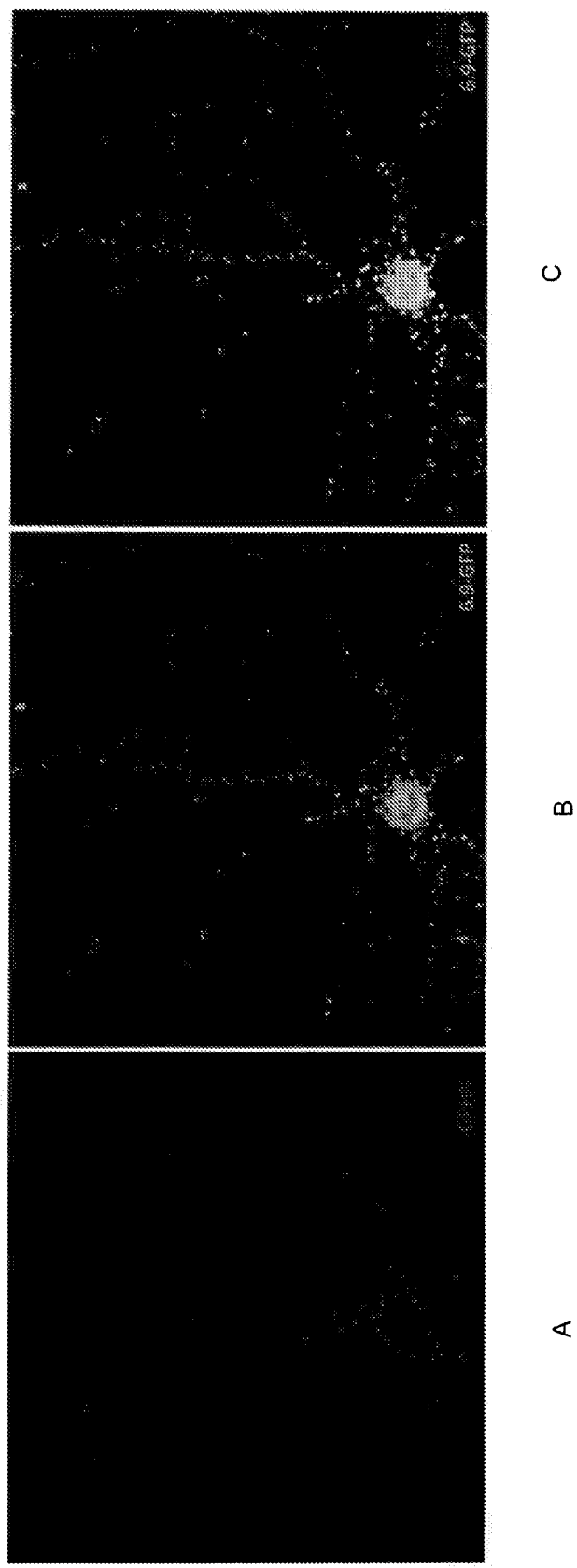
FIGS. 13A-C show that GFP-tagged anti-Gephyrin intrabody colocalizes perfectly with endogenous Gephyrin following expression in cortical neurons in culture.
Figure 14:
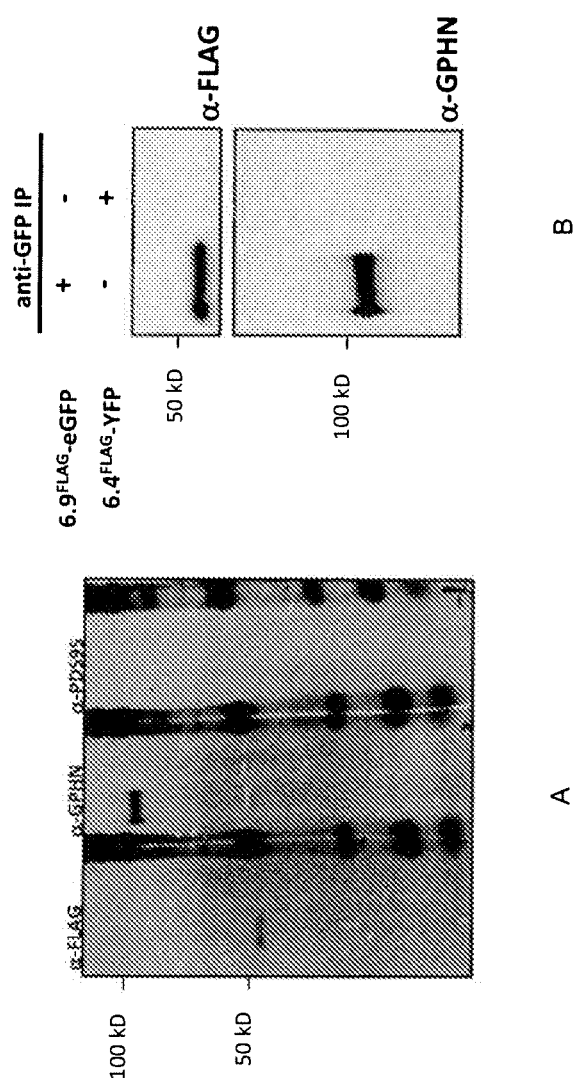
FIGS. 14A-B show that endogenous Gephyrin in cortical neurons co-immunoprecipitated with 6.9. Thus, intrabody bound with high specificity and affinity to endogenous PSD-95 or Gephyrin.

The GFP-tagged anti-Gephyrin intrabody colocalizes perfectly with endogenous Gephyrin following expression in cortical neurons in culture (FIG. 13). Immunoprecipitation and possibly biacore showed that the intrabody bound with high specificity and affinity to endogenous Gephyrin or, in a separate case, PSD-95 (FIG. 14).

Note with this assay numerous intrabodies can be tested in parallel. In particular, up to 50 intrabodies in a single experiment have been tested using this method.

This method has been used to generate intrabodies that bind at very high affinity and specificity in vivo to four different target proteins: Gephyrin, PSD-95, Calcium Calmodulin Kinase 2 alpha (CAMKIIa) and CAMKIIb. These intrabodies performed extremely well in assays where they labeled, or ablated their target proteins.

Example 3—Labeling Endogenous Protein with an Intrabody

To generate intrabodies, mRNA display, an in vitro protein selection method previously to produce peptides and proteins that bind targets with nanomolar to picomolar affinity (Roberts R W, Szostak J W (1997) RNA-peptide fusions for the in vitro selection of peptides and proteins. Proc Natl Acad Sci USA 94:12297-12302), was used (see Example 1).

Figure 15:
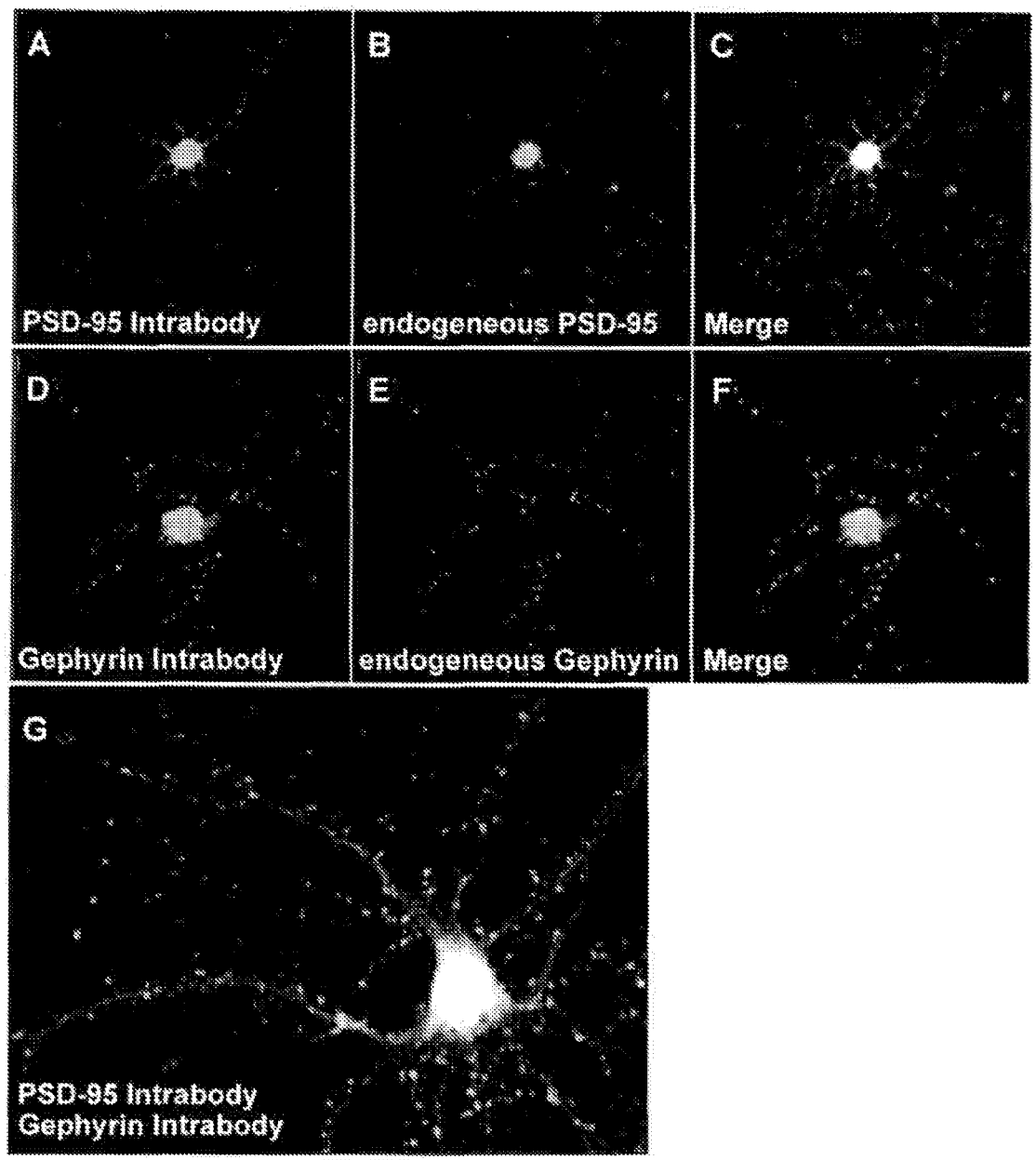
FIGS. 15A-G show cortical neurons expressing intrabodies (A, D), counterstained for their endogenous targets (B, E), and merges of the two (C, F). (G) Neuron coexpressing an intrabody against Gephyrin (dark gray) and a second against PSD-95 (light gray).

Gephyrin and PSD-95, scaffolding proteins that are localized to inhibitory and excitatory postsynaptic sites, respectively, were used as targets in two separate mRNA selection procedures (see procedure in Example 2). In both cases intrabodies that bind very tightly and specifically to the target proteins (FIG. 15). Using biochemical methods it was estimated that the Kds for both intrabodies are ~50 µM, indicating that they bind with better affinities than the best monoclonal antibodies.

When expressed in cortical neurons in culture, each intrabody was almost perfectly colocalized with its target as judged by immunocytochemistry (FIG. 15). When coexpressed in the same neuron the PSD-95 and Gephyrin intrabodies label distinct puncta which correspond to excitatory and inhibitory postsynaptic sites, respectively. Thus, intrabodies can label endogenous proteins in living neurons with very high fidelity. Furthermore, they allowed for labeling in living neurons.

Figure 5:
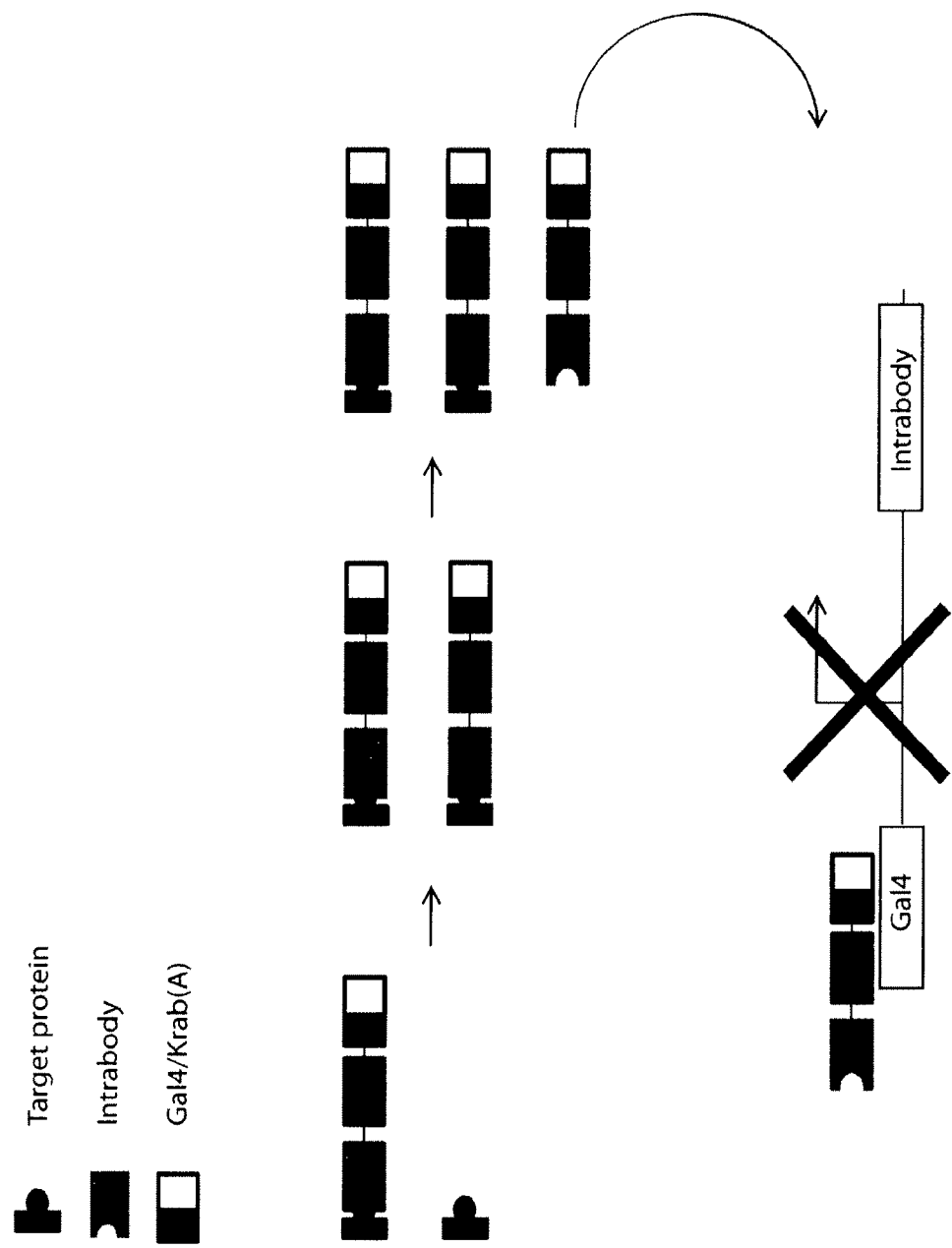
FIG. 5 is a schematic of transcriptional control system for intrabodies. The intrabody is fused with a Gal4/Krab(A) transcription factor. Excess intrabody goes to the nucleus where the Gal4/Krab(A) domain turns off transcription of the intrabody.
Figure 6:
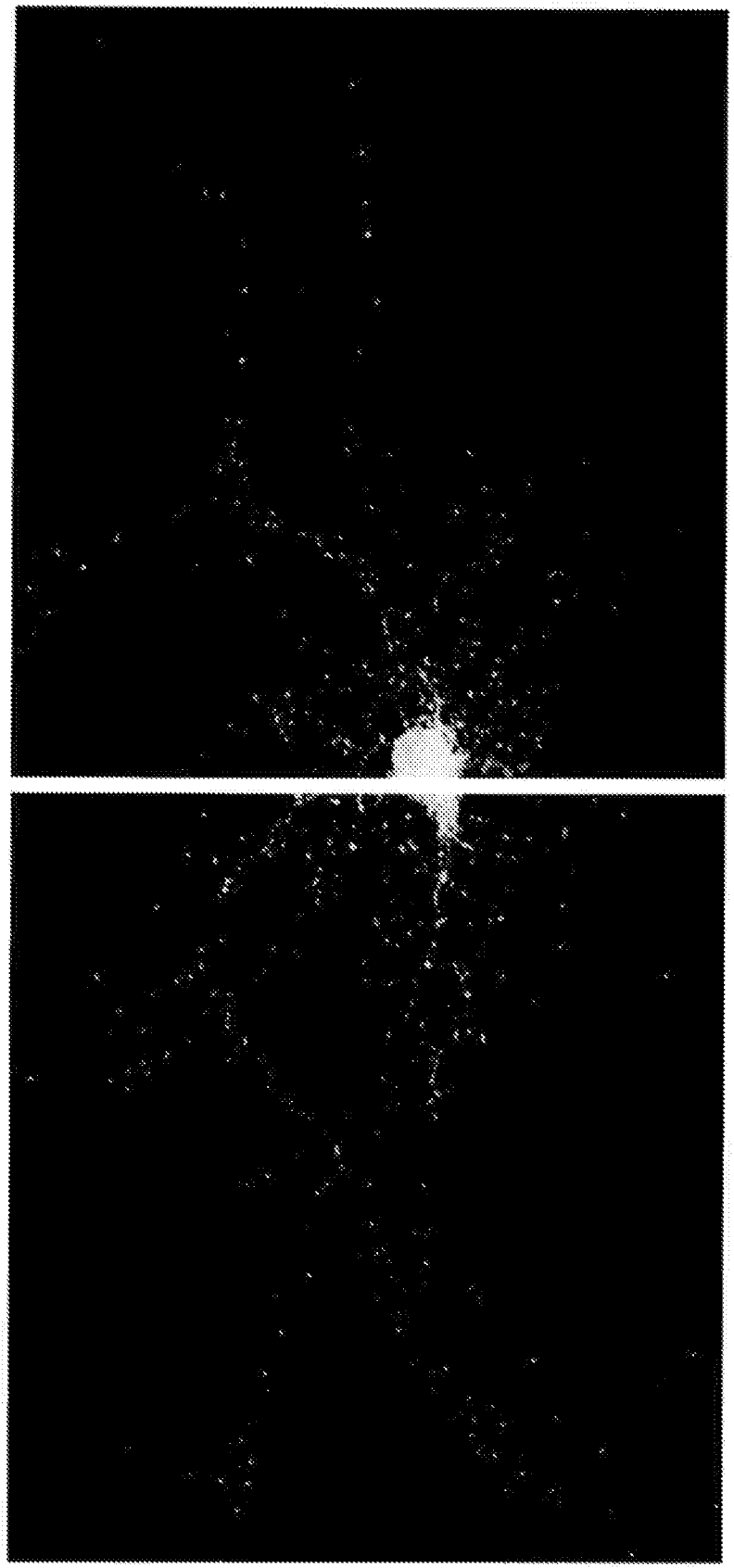
FIG. 6 shows cortical neuron expressing anti-PSD95 intrabody (light gray) and anti-Gephyrin intrabody (dark gray) with the transcriptional regulation system that insures that the level of intrabody matches the level of endogenous target.

An additional requirement for intrabodies is that they be expressed at precisely the same level as their endogenous target proteins to avoid background staining To regulate intrabody expression, a feedback system was generated based on the GAL4 transcriptional repressor Krab-A (see illustration in FIG. 5). This system insures that transcription of the intrabody is maintained at a level that results in virtually no excess intrabody protein regardless of the strength of the promoter or the amount of plasmid transfected (FIG. 6). Further, it's shown that that this method can be used with at least two intrabodies to track two independent proteins in the same live cell (FIGS. 15G and 6).

Example 4—Ablating Endogenous Protein with an Intrabody

An intrabody capable to ablating an endogenous protein was generated by fusing the cDNA encoding the intrabody with a sequence encoding the RING domain of X-linked inhibitor of aptosis protein (XIAP) (Tsai D E, et al. (1991) U1-snRNP-A protein selects a ten nucleotide consensus sequence from a degenerate RNA pool presented in various structural contexts. Nucleic Acids Research 19:4931-4936).

Following expression of the intrabody construct, for approximately 72 hours, between 90 and 95% of the target protein is ablated, without affecting other proteins or the health of the cell. Expression of the ablating intrabody caused Gephyrin specifically degraded 72 hours following transfection (FIG. 16-19). Importantly, there appeared to be no disruption of non-target proteins of neuronal morphology, indicating that this is a fast, efficient and specific method for down-regulating proteins.

Example 5—Ablation of CAMKIIalpha with a Targeting Intrabody

Figure 20:
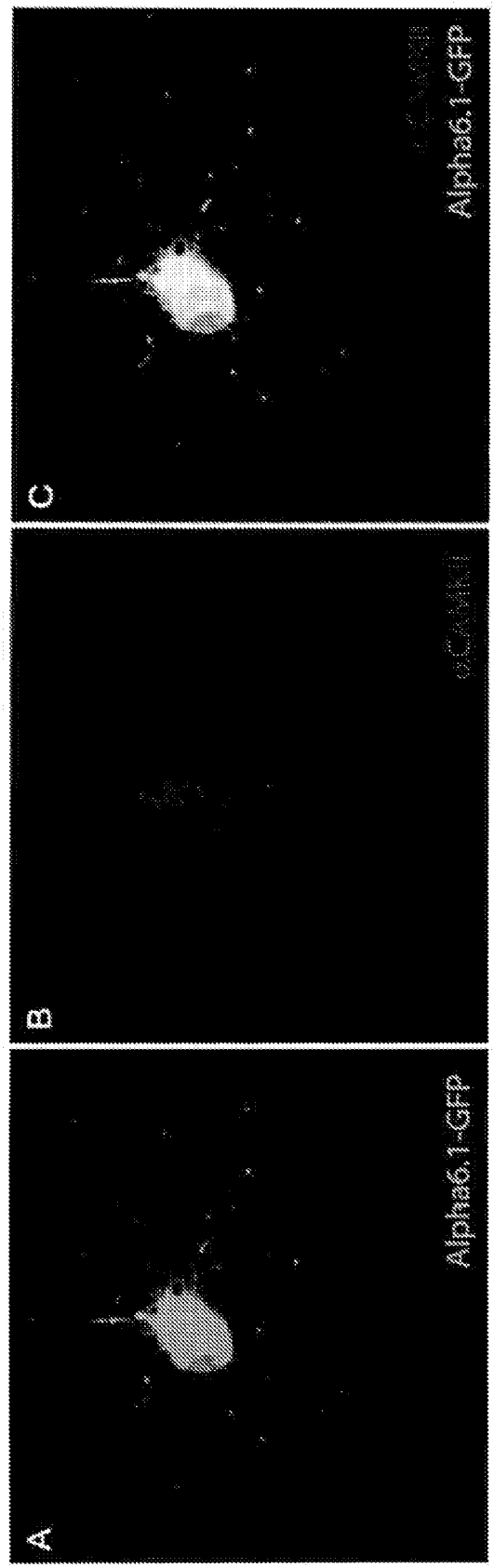
FIGS. 20A-C show Alpha6.1-GFP (A) expressed in dissociated cortical neurons in culture for 14 hours expresses in a pattern identical to that of endogenous CAMKIIa (B, C).

An intrabody against CAMKIIa (Alpha6.1) was selected with methods provided above. This intrabody colocalized precisely with its endogenous target protein when expressed in cortical neurons in culture (FIG. 20).

Figure 21:
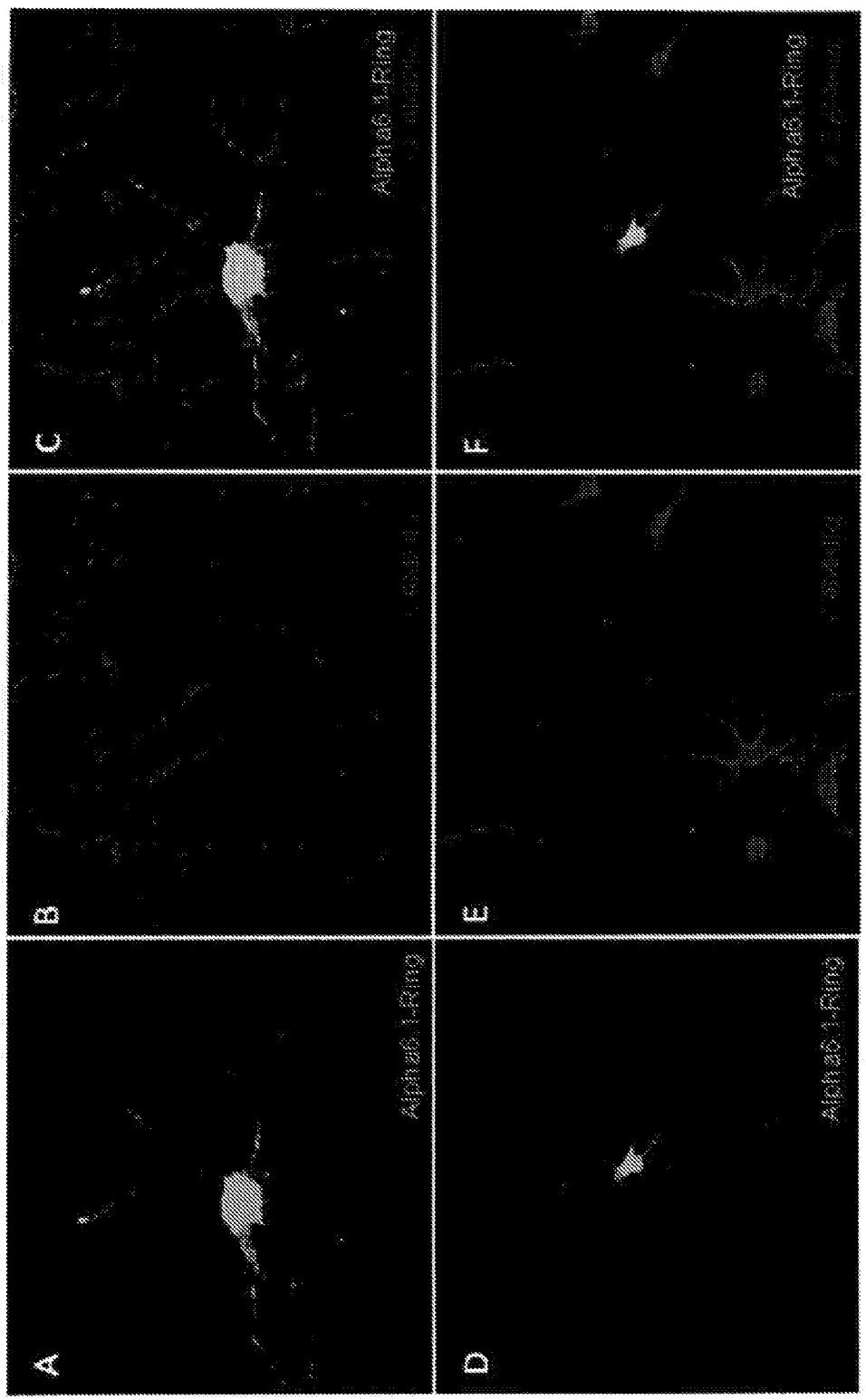
FIGS. 21A-F show (A, D) Alpha6.1-RING, an ablating intrabody against CAMKIIa expressed in cortical neurons in dissociated culture. FIGS. (B, C, E, F) CAMKIIa is completely ablated in neurons expressing Alpha6.1-RING.

To test the ability of a CAMKIIa intrabody, alpha6.1, to mediate protein ablation, it was fused it to the Ring domain from XIAP (to give Alpha6.1-RING) and was expressed in dissociated cultures of cortical neurons for 72 hours. It was found that Alpha6.1-RING caused almost complete degradation of endogenous CAMKIIa in a majority of transfected neurons (FIG. 21).

Example 6—Ablation of Gephyrin Following Lentiviral-Mediated Infection of Ablating Intrabody Against Gephyrin This example demonstrates the effectiveness of transcriptional control system for regulating intrabody expression.

Figure 22:
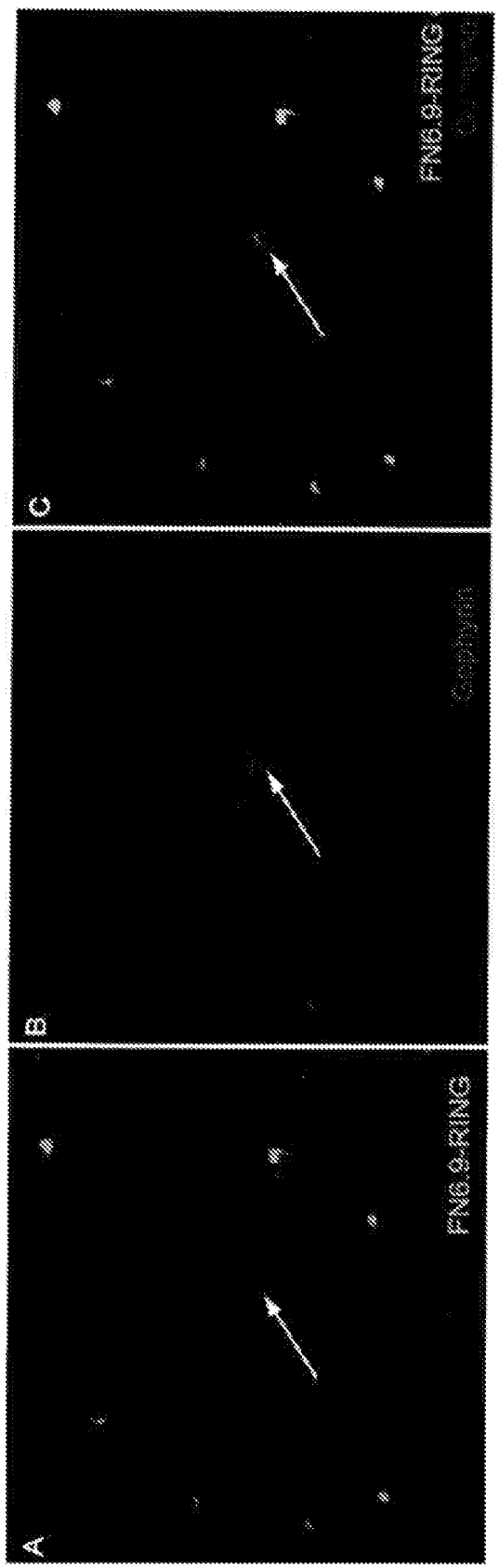
FIGS. 22A-C show FN6.9-RING, an ablating intrabody infects 7 of 8 cortical neurons in dissociated culture in a low power field. Arrow points to uninfected neuron. (B) Enodgenous Gephyrin is virtually absent from the processes of all infected neurons, but is highly expressed in uninfected neuron (arrow). (C) Merge of (A) and (B).

To further test for the efficiency of protein ablation mediated by the ablating intrabody against Gephyrin (FN6.9-RING) cortical neurons in culture was infected with lentivirus containing FN6.9-RING for 72 hours. Following fixation and staining for GFP and endogenous Gephyrin it was found that approximately 90% of neurons were infected and of those most expressed only very low levels of Gephyrin that was confined to the cell body (FIG. 22).

In previous examples it was found that expressing the anti-Gephyrin intrabody (FN6.9-GFP) without transcriptional control for approximately 14 hours in cortical neurons in culture resulted in its expression level matching the expression level of endogenous Gephyrin. To test the transcriptional control system FN6.9-GFP was expressed with transcriptional control for 7 days. In addition, these cells were cotransfected with a control RNAi construct (FIG. 16).

After fixation and staining for endogenous Gephyrin as well as for FN6.9-GFP it was found that the expression pattern of FN6.9-GFP overlapped that of endogenous Gephyrin almost 100% (FIG. 16) indicating that the expression of FN6.9-GFP precisely matched that of endogenous Gephyrin. This result is quite remarkable, because without transcriptional control intrabodies expressed for 1 week were expressed at a level many times that of endogenous Gephyrin (data not shown).

Figure 16:
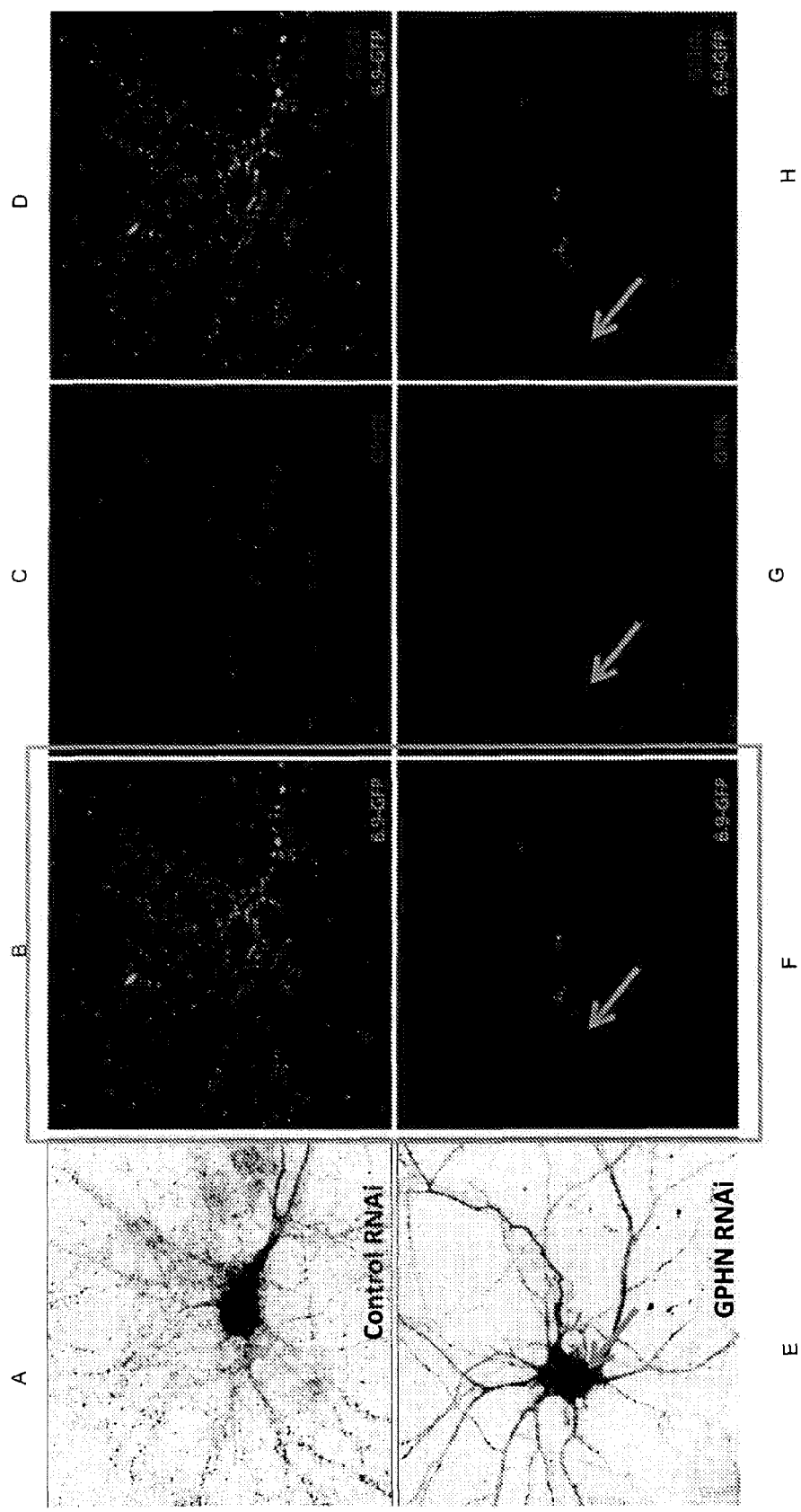
FIGS. 16A-H show that RNAi-mediated knockdown of endogenous gephyrin caused loss of 6.9 localization/signal in cortical neurons. To demonstrate the effectiveness of this system the anti-Gephyrin intrabody was expressed with expression control in neurons in culture. Normally they were expressed for about 14 hours in order to match the expression level of Gephyrin. Any more time and the amount of intrabody overwhelmed the amount of target. In this case the anti-gephyrin intrabody was expressed for 7 days. The figure shows that its localization precisely matched that of the endogenous Gephyrin with no background. At the same time this intrabody construct was coexpressed along with siRNA against Gephyrin. The net effect of the siRNA was to dramatically reduce the level of Gephyrin expression in the neurons. As shown, the regulated intrabody precisely labeled the endogenous Gephyrin in this cell even though its expression level is only about 1/50$^{th}$ that of the cell above it. Thus, the expression level of the intrabody precisely matched that of the endogenous protein regardless of the expression level of that protein.
Figure 17:
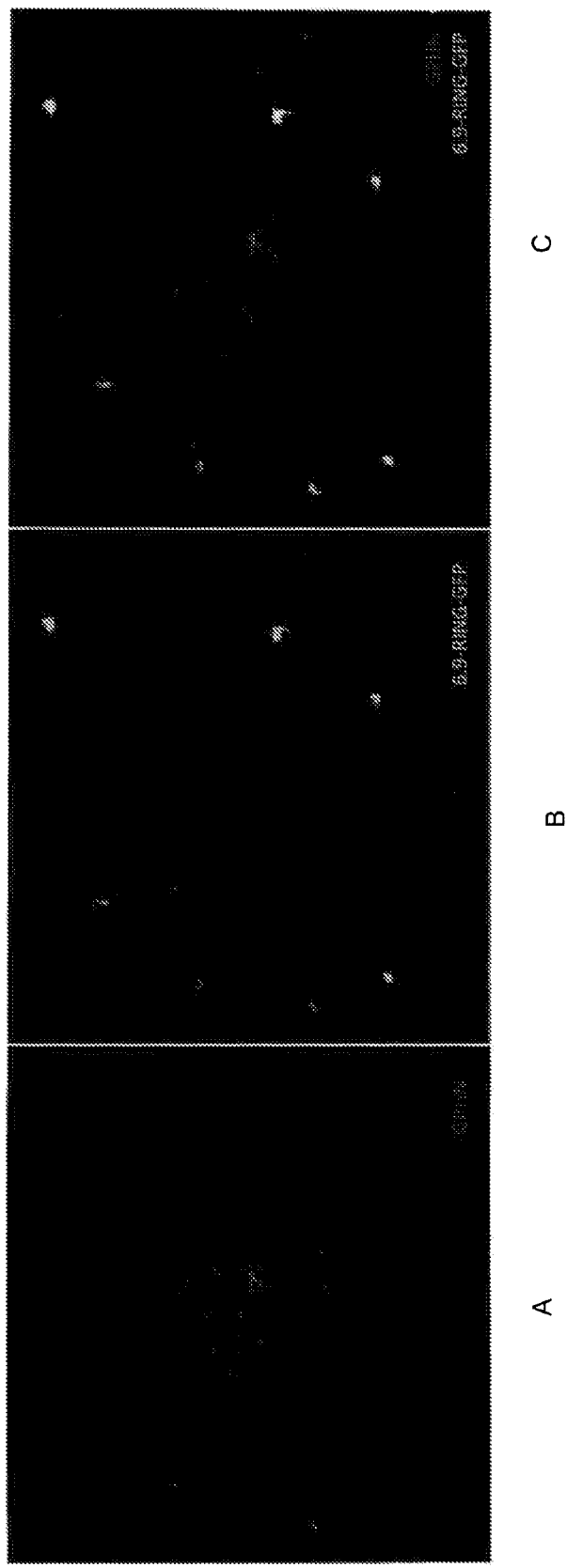
FIGS. 17A-C show that fusion of the RING domain from XIAP to fibronectin 6.9's C-terminus resulted in decreased endogenous GPHN in cortical neurons. The anti-Gephyrin intrabody fused to the E3 ligase was expressed in cortical neurons in culture using lentivirus. After 72 hour, it was found that endogenous Gephyrin expression in cortical neurons was profoundly downregulated in virtually all cells where the intrabody fusion was expressed. This is illustrated in the figure with 8 neurons. Seven are infected with the virus and showed very little staining for endogenous Gephyrin (left panel). In contrast the 8$^{th}$ expresses little or no intrabody and expresses a normal amount of Gephyrin. In control experiments where the intrabody itself with no degradation domain was expressed, there was no effect on expression of Gephyrin.
Figure 18:
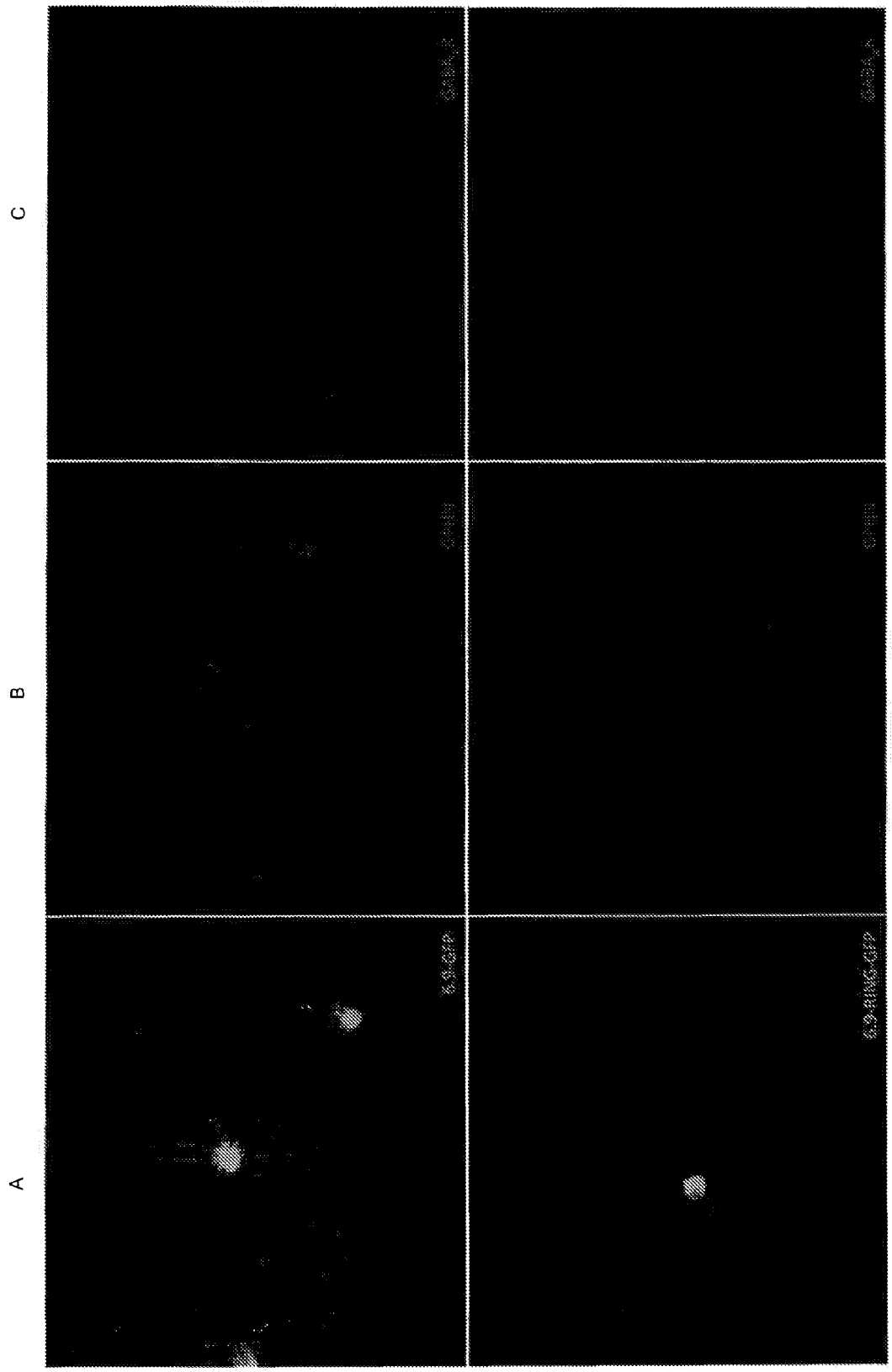
FIGS. 18A-F show that Fn6.9-RING ablated Gephyrin but not GABA$_A$R. In the figure, a neuron expressing the anti-Gephyrin intrabody was costained for the GABA receptor. The GABA receptor was still largely present, and although it was expressed in a less punctuate manner than in control neurons, it would seem that at least some of the synaptic structure has been preserved. This result is consistent with the intrabodies being able to literally pluck the Gephyrin from the structure of the postsynaptic inhibitory site without destroying its structure.
Figure 19:
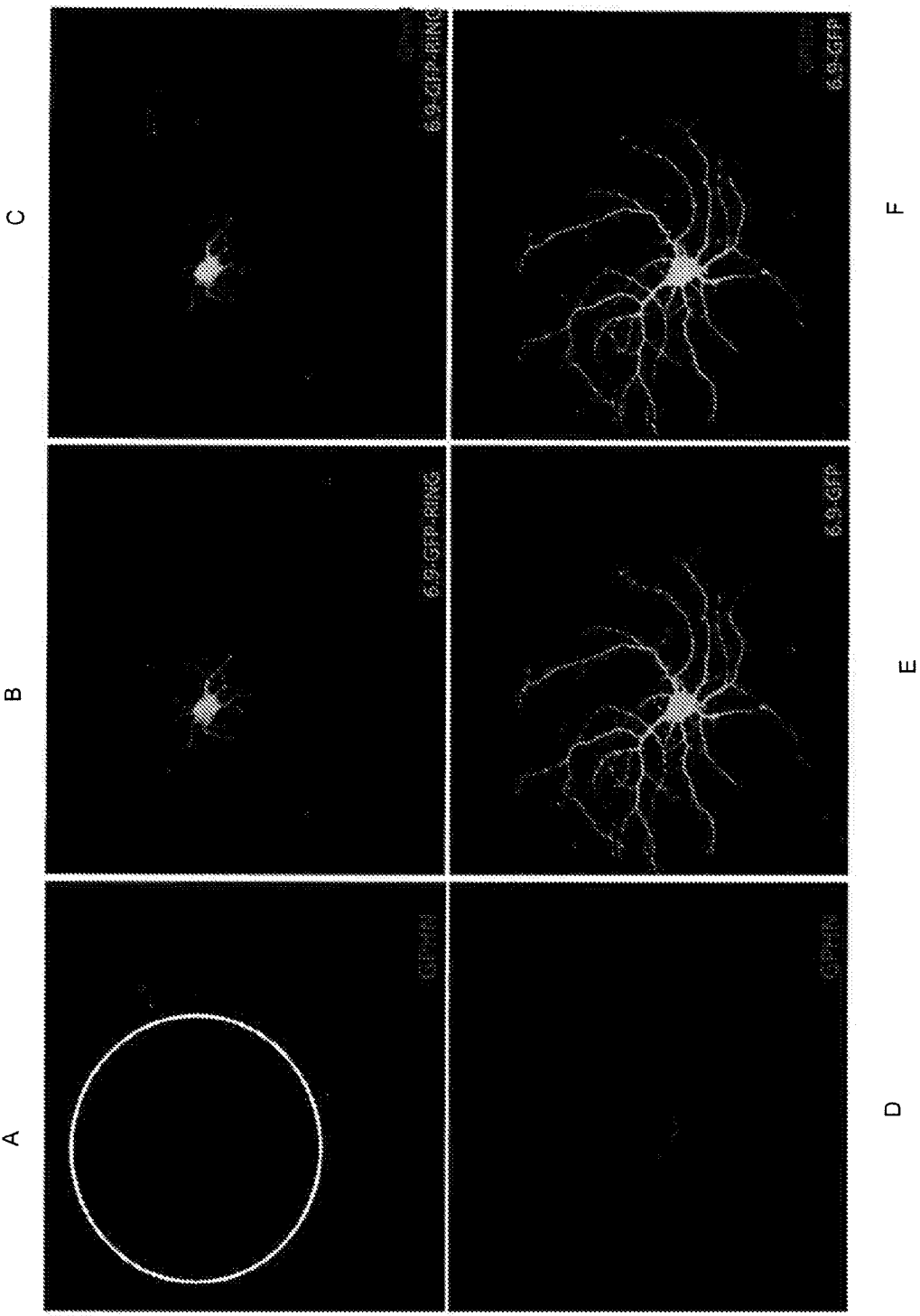
FIGS. 19A-F show that fusion of the RING domain from XIAP to fibronectin 6.9's C-terminus resulted in decreased endogenous GPHN in cortical neurons.

In addition, FN6.9-GFP was coexpressed with transcriptional control along with RNAi against Gephyrin (FIGS. 16 E-H). The RNAi had the effect of dramatically reducing the expression level of endogenous Gephyrin (FIG. 16G). Remarkably, FN6.9-GFP perfectly colocalized with Gephyrin indicating that its expression level matched that of Gephyrin (FIGS. 16 G, H) even though Gephyrin was expressed at a level much lower than it was in the presence of control RNAi (FIGS. 16 C, D).

Example 7—Transcriptional Control Using Zinc Finger DNA-Binding Domains

In this example, the GAL4 binding domain was substituted with a Zinc Finger binding domain (gtcatcctcatc), which is known to be a monomer. In particular the CCR5 left handed Zinc finger was used, which binds to a specific 16 nucleotide sequence in CCR5, a gene that not expressed in neurons. The Zinc Finger/Krab(A)-mediated transcriptional control was shown to effectively control expression in two different contexts. Both PSD-95 and Gephyrin intrabodies, when regulated using the Zinc Finger-based transcriptional control system, labeled their target molecules with very little background.

Example 8—Intrabody-Mediated Cell Specific Expression

It is possible to precisely regulate the level of intrabody expression so that it matches that of the target by using the Zinc finger transcriptional control system it. Thus, in cells in which there is no target there should be no intrabody. To test this, Applicants coexpressed the PSD-95 intrabody regulated by the Zinc finger/Krab(A) transcriptional control system with HA-mCherry expressed under a constitutive promoter. Note that PSD-95 is expressed only in neurons and not in glial cells. Therefore, it was not expected that HA-mCherry would be seen in both neurons and glia, but rather Applicants expected that the intrabody would only be expressed in neurons and not in glia. Remarkably, neurons expressed both the intrabody and mCherry and glia expressed only mCherry. This result shows that intrabodies can be used to express heterologous proteins in a cell specific manner by fusing the open reading frame (ORF) of the heterologous gene to the intrabody via a T2A autocleavage site. So, for instance, if the heterologous gene were fused to the PSD-95 intrabody via T2A it would be expressed solely in neurons and not in glia.

Example 9—Gephyrin E3 Ligase-Mediated Degradation

Figure 23:
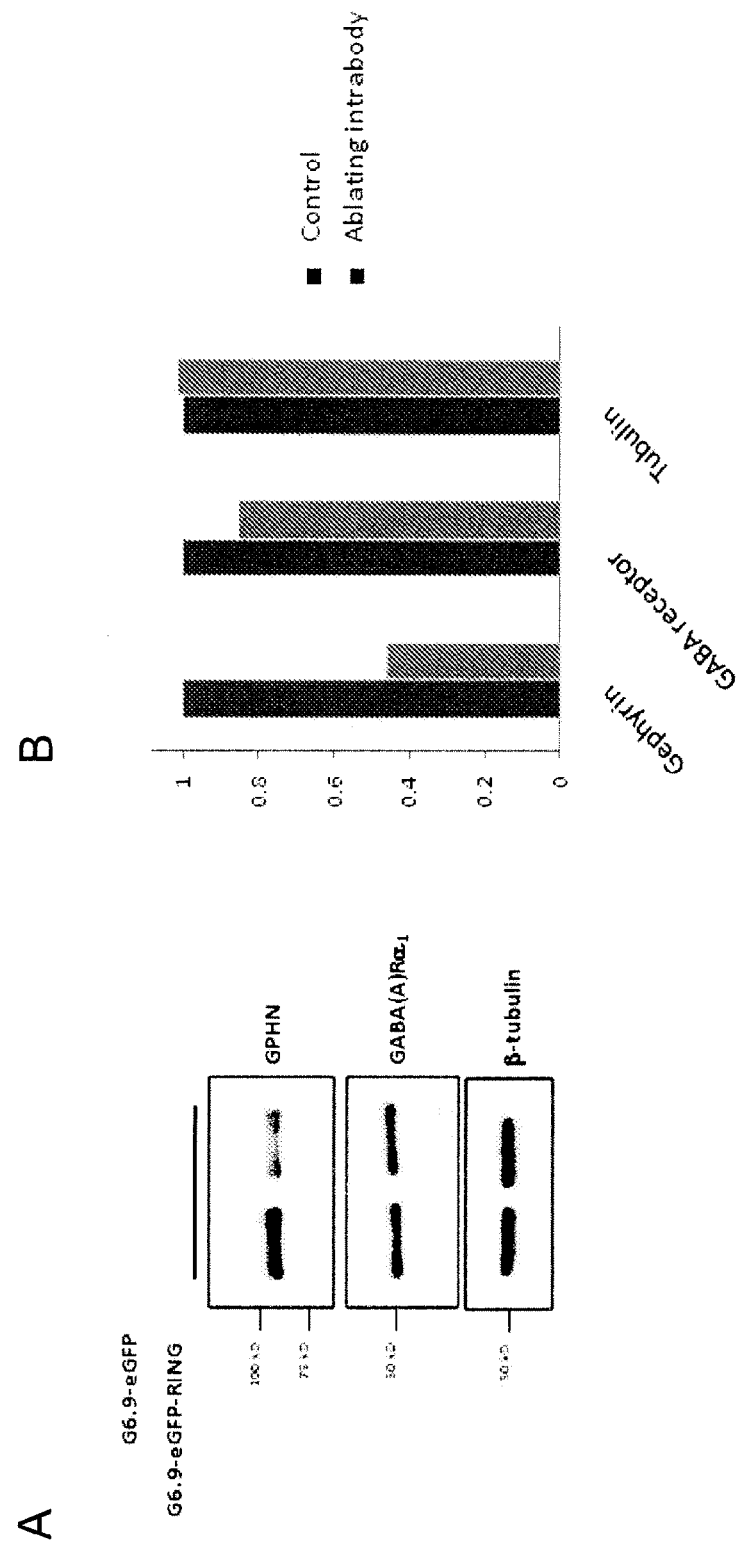
FIG. 23A-B show Gephyrin intrabody fused to a Ring domain from XIAP (G6.9-eGFP-RING) expressed in cortical neurons in culture following lentiviral infection causes a 55% decrease in the amount of endogenous Gephyrin and a 15% decrease in the amount of GABA receptor, indicating that degradation is specific.

A fusion of the E3 ligase from XIAP to the Gephyrin intrabody causes the rapid degradation of endogenous Gephyrin. To test the efficacy of degradation, a lentiviral vector was constructed that expresses the Gephyrin intrabody-XIAP E3 ligase in approximately 60% of cells in dissociated neuronal cultures. These cultures were infected for 72 hours and then lysates were collected run on gels to determine the degree of protein degradation. Approximately 55% of the Gephyrin was degraded, which correlates to the approximate percentage of cells that were infected. Furthermore, there was only a 15% drop in the amount of GABA receptor. See FIG. 23. This demonstrates remarkable specificity since the GABA receptor and Gephyrin form a complex. Furthermore, the specificity here may be underestimated because elimination of Gephyrin destabilizes the GABA receptor complex causing a drop in expression. Yu, W., et al. (2007) Mol Cell Neurosci. 36(4):484-500.

Example 10—Intrabodies Controlling Expression of Heterologous Genes

Figure 24:
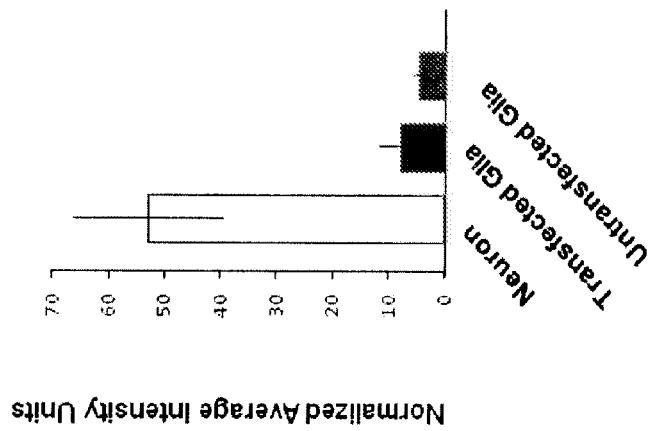
FIG. 24A-B show PSD-95 FingR coexpressed with HAmCherry in neuron and glia. PSD-95 FingR expresses in neuron, but not in glial cell, matching the cell-specific expression pattern of PSD-95. Note that PSD-95 FingR did not express in glial cells at rate that was significantly above background staining.
Figure 24:
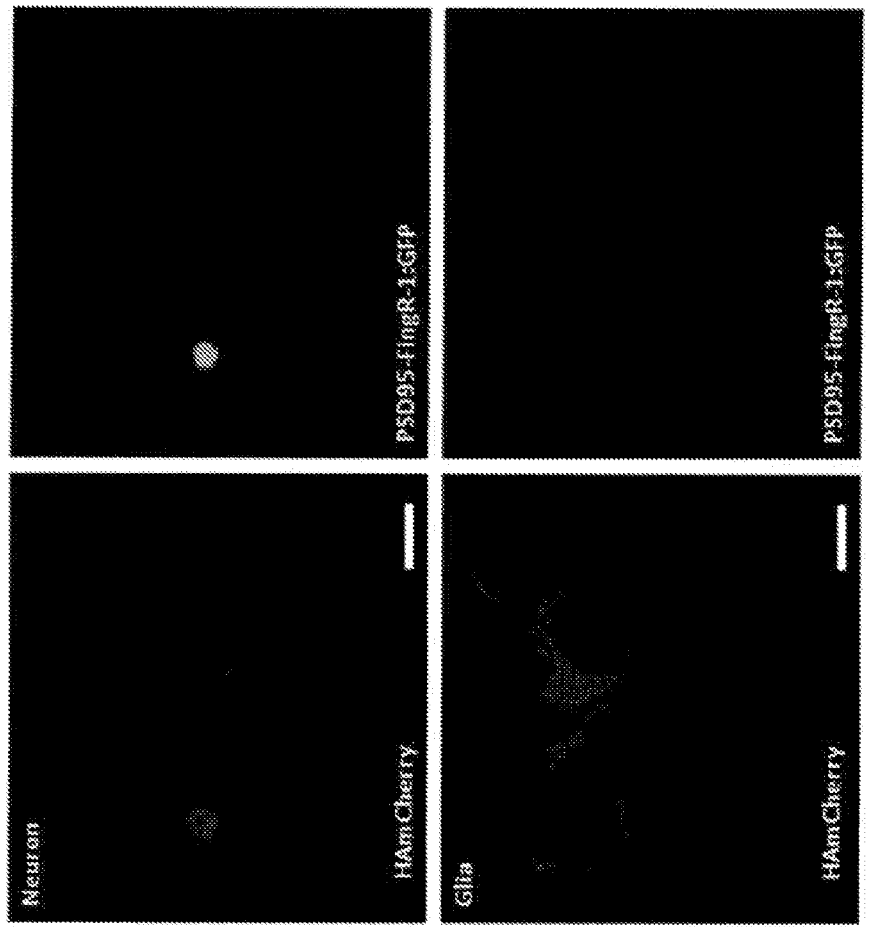

Because the transcriptional regulation system matches the level of PSD-95 to that of its endogenous target, its expression should be suppressed in cells that do not make PSD-95. Applicants' cultures contain neurons, which express PSD-95, and glia, which do not (Hunt, C. A., et al. (1996) 16(4):1380-8), serving as a perfect system to test this hypothesis. Accordingly, Applicants expressed PSD-95 Intrabody-GFP (also called PSD-95.FingR-GFP), along with mCherry to identify transfected cells, in cultures made from rat cortex and then compared the staining patterns of the two proteins in neurons and glia. As expected mCherry was expressed in both neurons and glia, and 100% of cells that expressed PSD-95.FingR-GFP also expressed mCherry (n=58). Remarkably, while PSD-95.FingR-GFP was robustly expressed in transfected (mCherry-positive) neurons (59+/−12 a. u., n=10; FIG. 24 A, B), virtually no GFP was detected in transfected glial cells (9+/−6 a.u., n=10) compared with a background of 12+/−11 a. u., n=10 for untransfected cells (FIG. 24). These data indicate that expression of PSD-95.FingR-GFP was highly restricted to neurons. Thus, the expression of transcriptionally controlled PSD-95.FingR-GFP is confined to the same cell types as is endogenous PSD-95. This result suggests that when the target protein is expressed in a cell-specific manner, the transcriptional control system causes the FingR to be expressed with cell specificity as well.

Figure 25:
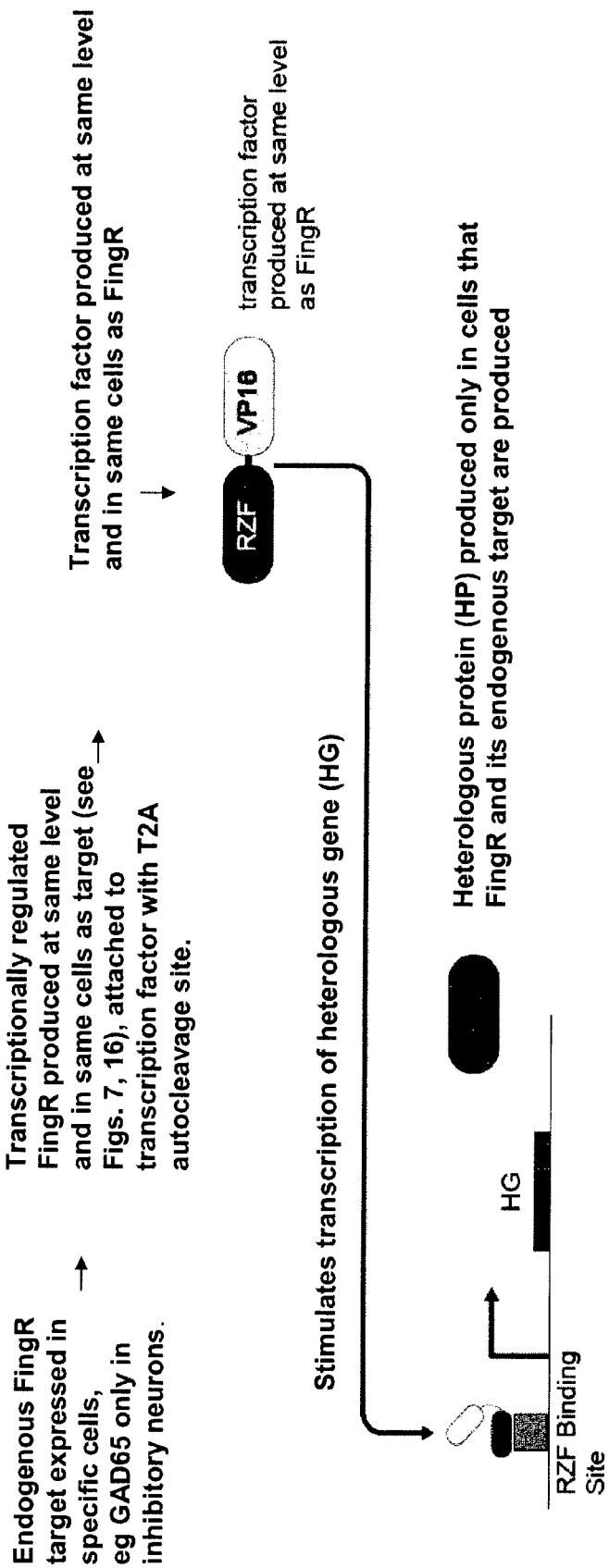
FIG. 25 illustrates transcriptional control system to produce FingR and a transcription factor, RZF-VP16 at exactly the same expression level and in the same cells as the endogenous target protein of the FingR. RZF-VP16 will then cause transcription of a heterologous gene (HG) and a heterologous protein (HP) in the same cells that the FingR target protein is expressed within.

Applicants have shown that transcriptionally controlled FingRs express at precisely the same level, and only in the same cells, as their endogenous target proteins when regulated with a transcriptional control system. To express heterologous proteins in a regulated manner, Applicants expressed a transcription factor at precisely the same level as a FingR by joining the two with a T2A autocleavage site. de Felipe, P., et al. (1999) Gene Ther. 6(2):198-208. This transcription factor will interact with a binding site on a second construct causing expression of a gene encoding a heterologous protein (FIG. 25). Note that the heterologous gene is downstream of a minimal promoter that cannot mediate transcription autonomously. The transcription factor will be produced only in cells that express the target of the FingR, and thus the heterologous protein will also be produced only in those cells. The system will consist of two constructs: 1. PSD-95.FingR fused via a T2A site to a transcription factor consisting of a right-handed zinc finger DNA binding domain fused to a VP16 transcriptional activator. 2. A minimal promoter fused to a right-handed zinc finger DNA binding site driving the expression of heterologous protein, mKate.

Example 11—PSD-95 Intrabody-MDM2 Degrades Endogenous PSD-95

Figure 26:
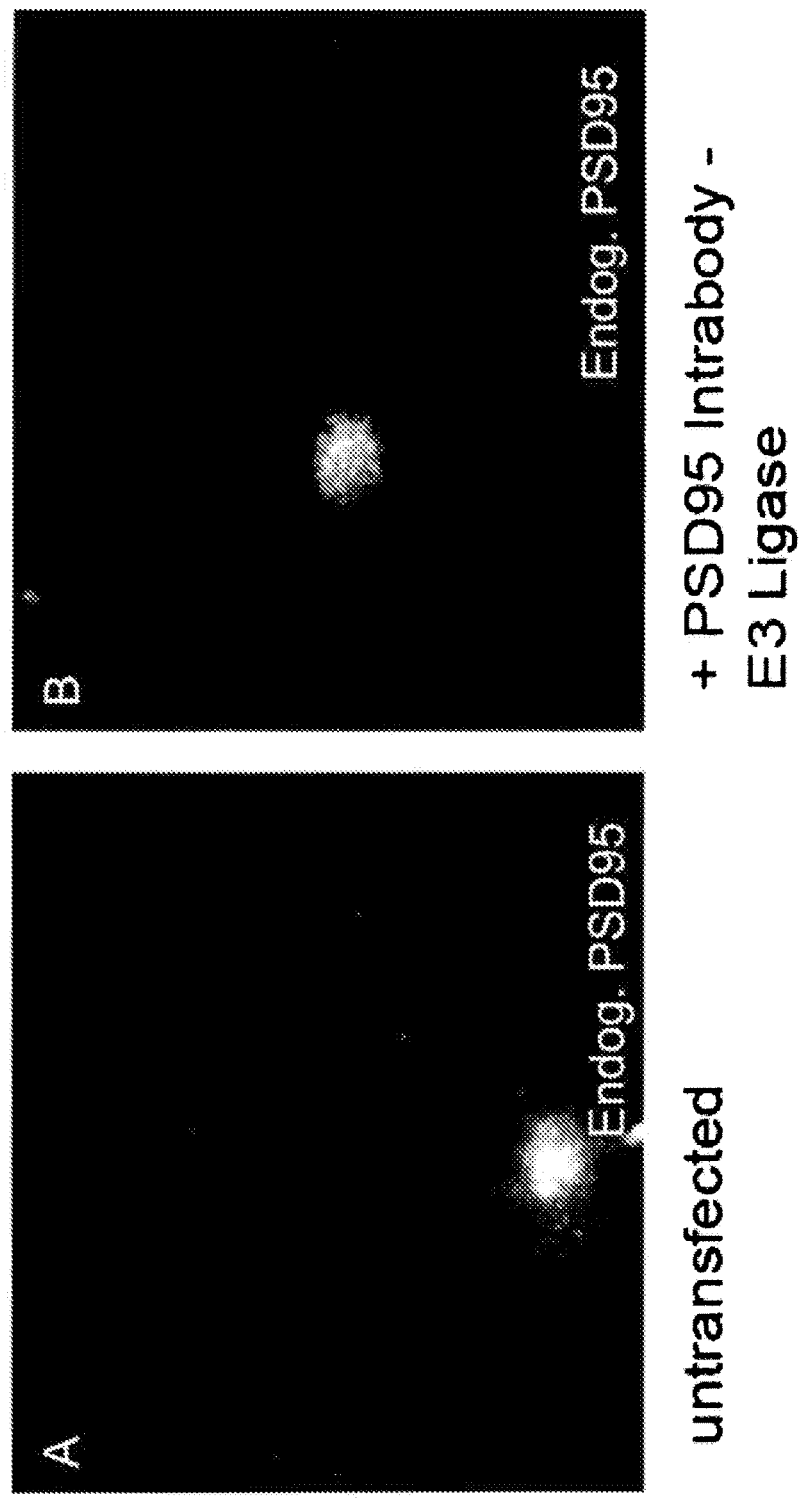
FIGS. 26A-B illustrate endogenous PSD-95 in an untransfected neuron (A) and in a neuron expressing PSD-95 Intrabody-E3 Ligase for 10 hours (B).

In order to mediate specific degradation of PSD-95, Applicants fused the PSD-95 intrabody with the E3 ligase domain from MDM2 (Murine Double Minute, amino acids 403-458), which is responsible for ubiquitinating PSD-95 (Perez-Gonzalez, J. A. and J. Vara, (1983) Biochem. Biophys. Res. Commun. 113:772). By placing the E3 ligase onto the PSD-95 intrabody, Applicants created a protein that specifically and efficiently degrades PSD-95. In particular, expression of this construct for 24 hours in cortical neurons in dissociated culture results in the complete elimination of immunostaining of endogenous PSD-95 in the processes of transfected cells (FIG. 26).

Example 12—A Rapamycin-Dependent Inducible PSD-95 Intrabody-Degron Degrades Endogenous PSD-95

Figure 27:
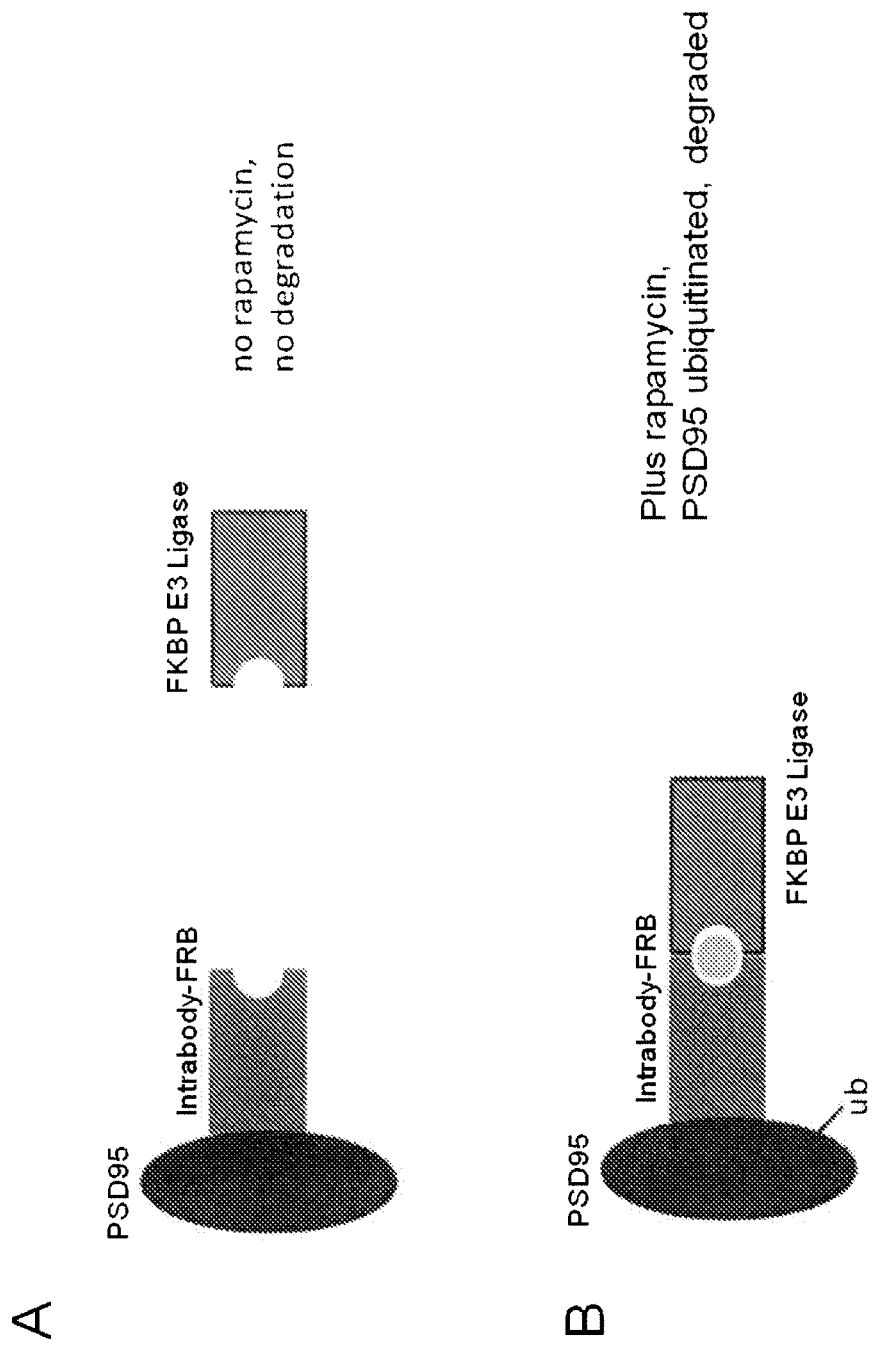
FIGS. 27A-B are schematics of inducible ablating intrabody that mediates fast and efficient degradation of endogenous PSD-95.

To make the PSD-95 intrabody-MDM2 construct inducible, Applicants fused the intrabody to a domain from FRB and the MDM2 E3 ligase to FKBP. Because FKBP, FRB and Rapamycin form a ternary complex (Chen, J., et al. (1995) Proc Natl Acad Sci USA 92(11): 4947-51), addition of a Rapamycin analog to the above constructs causes the PSD-95 intrabody to associate with the E3 ligase domain of MDM2 (FIG. 27). Addition of iRap (a Rapamycin analog) to cells expressing PSD-95 intrabody-FRB and FKBP-MDM2 E3 ligase causes immediate degradation of endogenous PSD-95. FIG. 27A shows neurons expressing PSD-95 intrabody-FRB and FKBP-MDM2 E3 ligase before addition of iRap, and PSD-95 is expressed robustly. However, 2 hours after addition of iRap similar cells show a very low expression of endogenous PSD-95 (FIG. 27B). Thus, using this system it is possible to degrade an endogenous protein efficiently, quickly and inducibly. Furthermore, this system is compatible with a caged Rapamycin analog (Karginov, A. V. et al. (2010) J Am Chem. Soc. 28:743) that will allow degradation of endogenous proteins to be light activated.

Figure 28:
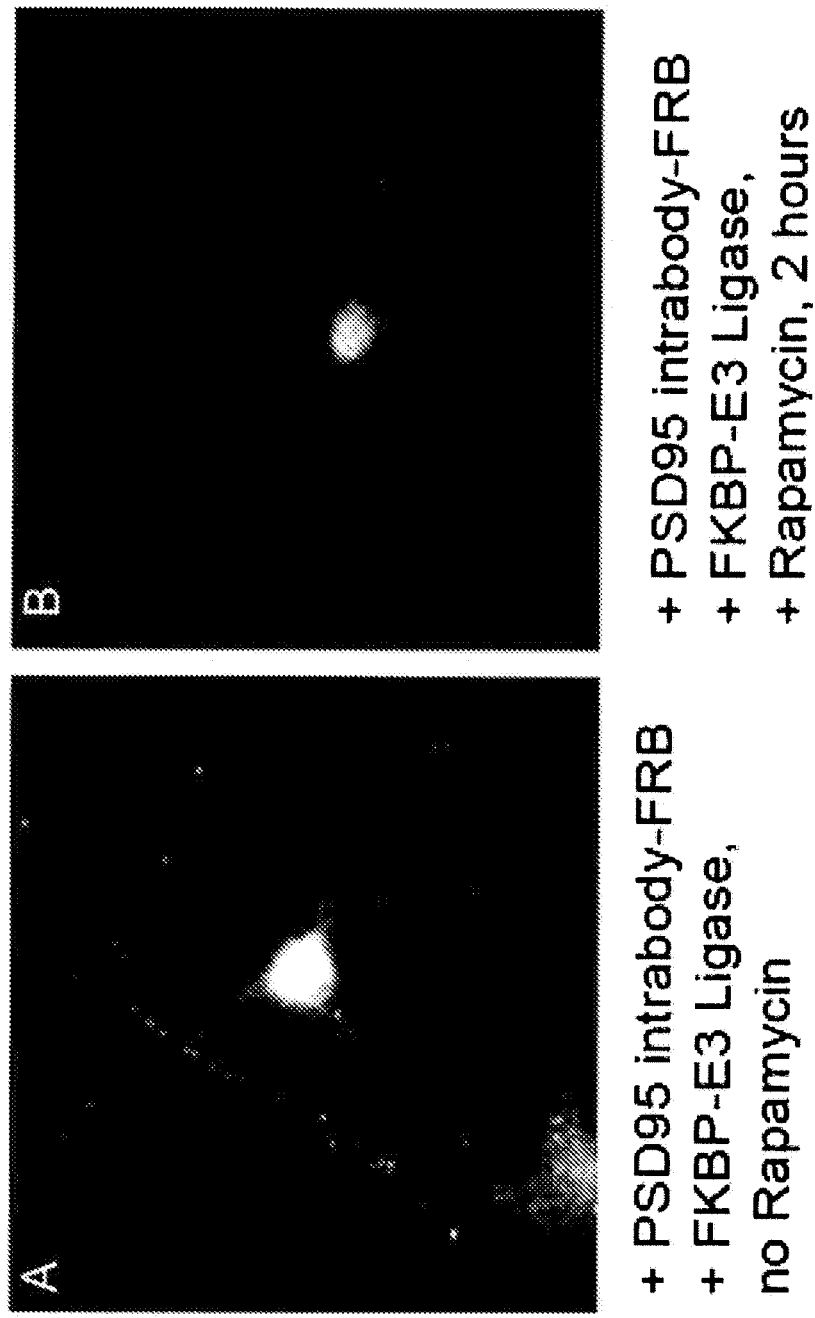
FIGS. 28A-B show endogenous PSD-95 staining in an untransfected neuron (A) and a neuron expressing PSD-95 intrabody-FRB+ FKBP-E3 Ligase with no Rapamycin (B) showing normal amounts of endogenous PSD-95.
Figure 29:
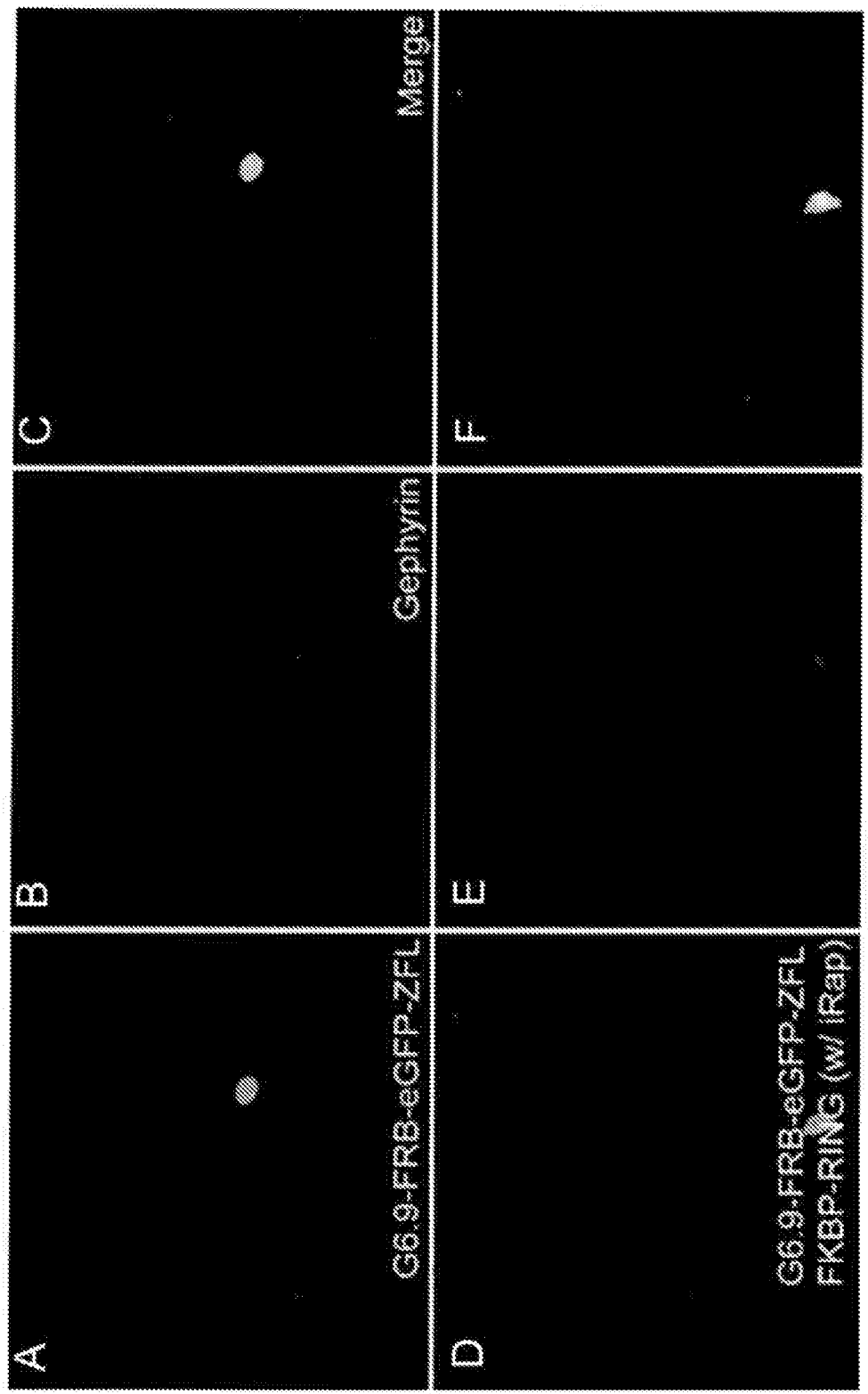
FIGS. 29A-F. (A) Gephyrin intrabody (G6.9) fused to FRB colocalizes with endogenous Gephyrin (B, C) following expression in cortical neurons in culture for 4 days without addition of iRap. (D-F). Addition of iRap for 10 hours causes elimination of Gephyrin puncta (E).

Applicants also created a Rapamycin-inducible intrabody construct that mediates degradation of Gephyrin. As with the PSD-95 directed construct it consists of a Gephyrin intrabody fused to FRB and the E3 ligase from XIAP fused to FKBP. In the absence of iRAP, this construct does not cause degradation of endogenous Gephyrin (FIG. 28). However, if iRAP is added then endogenous Gephyrin is degraded within 10 hours. A neuron expressing PSD-95 intrabody-FRB+

FKBP-E3 Ligase with Rapamycin for 2 hours showed efficient degradation of endogenous PSD-95.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

What is claimed is:

1. A polynucleotide comprising:
   (1) a nucleic acid sequence encoding a fusion polypeptide, wherein the fusion polypeptide comprises
      (a) a binding moiety for recognizing an endogenous protein, and
      (b) a transcription factor; and
   (2) a transcription regulatory element operatively linked to the nucleic acid sequence, wherein the transcription regulatory element regulates the transcription of the binding moiety and the transcription factor regulates the activity of the transcription regulatory element.

2. A system for the expression of two or more polynucleotides, the system comprising:
   (1) the polynucleotide of claim 1; and
   (2) a second nucleic acid sequence encoding a second fusion polypeptide comprising
      (a) a minimal promoter;
      (b) a transcription factor that mediates expression of the binding moiety; and
      (c) a heterologous protein; wherein the transcription factor regulates the minimal promoter causing expression of the heterologous protein.

3. The polynucleotide of claim 1, wherein the binding moiety is one or more of an antibody mimetic, an intrabody, an antigen binding fragment of an antibody, a natural ligand, a monobody, a linear peptide, a lipocalin scaffold, an affibody scaffold or a DARPin scaffold.

4. The polynucleotide of claim 3, wherein the intrabody comprises a fibronectin peptide.

5. The polynucleotide of claim 4, wherein the fibronectin peptide comprises a 10FnIII fragment.

6. The polynucleotide of claim 1, wherein the transcription factor comprises a DNA binding domain.

7. The polynucleotide of claim 6, wherein the transcription factor is Gal4, LexA or a zinc finger domain.

8. The polynucleotide of claim 7, wherein the transcription factor further comprises one or more of a regulatory domain, a transcriptional activator or an inducible promoter.

9. The polynucleotide of claim 7, wherein the transcription factor comprises a DNA binding domain of Gal4 and a regulatory domain of Krab(A).

10. The polynucleotide of claim 1, wherein the fusion polypeptide further comprises a reporter.

11. The polynucleotide of claim 10, wherein the reporter is a green fluorescent protein (GFP), a blue fluorescent protein (BFP), a cyan fluorescent protein (CFP), a yellow fluorescent protein (YFP), mCherry, dTomato, mPlum, mOrange, mCitrine, Ypet, Cerulean CFP, luciferase, or β-galactosidase.

12. The polynucleotide of claim 1, wherein the endogenous protein is a transmembrane protein, a nucleic protein, a cytoplasmic protein, a secreted protein, or an organelle protein.

13. The polynucleotide of claim 1, wherein the endogenous protein is a transmembrane protein.

14. A DNA construct comprising the polynucleotide of claim 1 and a vector.

15. A composition comprising the polynucleotide of claim 1 and a carrier.

16. An isolated cell comprising the polynucleotide of claim 1.

17. A method for labeling an endogenous protein in a cell, comprising contacting the cell with the polynucleotide of claim 10, wherein the endogenous protein is labeled with the reporter.

18. The polynucleotide of claim 1, wherein the fusion polypeptide further comprises a protein degradation signal.

19. A system comprising:
   (1) the polynucleotide of claim 18 and
   (2) a second nucleic acid sequence encoding a second fusion polypeptide comprising
      (a) a minimal promoter;
      (b) a transcription factor that mediates expression of the binding moiety; and
      (c) a heterologous protein; wherein the transcription factor regulates the minimal promoter causing expression of the heterologous protein.

20. The polynucleotide of claim 18, wherein the binding moiety comprises one or more of an antibody mimetic, an intrabody, an antigen binding fragment of an antibody, a natural ligand, a monobody, a linear peptide, a lipocalin scaffold, an affibody scaffold or a DARPin scaffold.

21. The polynucleotide of claim 20, wherein the intrabody comprises a fibronectin peptide.

22. The polynucleotide of claim 18, wherein the protein degradation signal induces protein degradation of a polypeptide encoded by the polynucleotide.

23. The polynucleotide or system of claim 22, wherein the protein degradation is through ubiquitination, lysosomal degradation, or autophagy.

24. The polynucleotide or system of claim 23, wherein the protein degradation is through ubiquitination.

25. The polynucleotide of claim 18, wherein the protein degradation signal is a ubiquitin ligase, a HECT domain of an E6 protein, C20-WW-HECT, a Ring domain of Der3/Hrd1, a B-box domain of a TRIM protein, a U-box domain, KFERQ having the sequence SEQ ID NO: 1, Arg12 or Atg8/LC3.

26. The polynucleotide of claim 25, wherein the ubiquitin ligase comprises one or more of a Ring domain of a protein X-linked mammalian inhibitor of apoptosis (XIAP), MDM2 or HDM2.

27. A DNA construct comprising the polynucleotide of claim 18 and a vector.

28. A composition comprising the polynucleotide of claim 18 and a carrier.

29. An isolated cell comprising the polynucleotide of claim 18.

30. A method for inhibiting an activity of or degrading an endogenous protein in a cell, comprising contacting the cell with the polynucleotide of claim 18, wherein the protein degradation signal causes the activity of the endogenous protein to be inhibited or degradation of the endogenous protein.

31. A composition comprising the polynucleotide of claim 10 and a second polynucleotide encoding a fusion polypeptide comprising a target peptide sequence and a cell localization domain, wherein the binding moiety recognizes the target peptide sequence.

32. A kit comprising the polynucleotide of claim 10 and a second polynucleotide encoding a fusion polypeptide comprising a target peptide sequence and a cell localization domain, wherein the binding moiety recognizes the target peptide sequence.

33. The composition of claim 31, wherein the binding moiety is one or more of an antibody mimetic, an intrabody, an antigen binding fragment of an antibody, a natural ligand, a monobody, a linear peptide, a lipocalin scaffold, an affibody scaffold or a DARPin scaffold.

34. The composition of claim 33, wherein the intrabody comprises a fibronectin peptide.

35. The composition of claim 34, wherein the fibronectin peptide comprises a 10FnIII fragment.

36. The composition of claim 31, wherein the cell localization domain localizes the chimeric polypeptide at Golgi apparatus, endoplasmic reticulum, lysosome, mitochondria, plasma membrane, or apical or basolateral domain of an epithelial cell.

37. The composition of claim 31, wherein the reporter comprises a green fluorescent protein (GFP), a blue fluorescent protein (BFP), a cyan fluorescent protein (CFP), a yellow fluorescent protein (YFP), mCherry, dTomato, mPlum, mOrange, mCitrine, Ypet, Cerulean CFP, luciferase, or β-galactosidase.

* * * * *